US012569574B2

(12) United States Patent  
Giacca et al.

(10) Patent No.: US 12,569,574 B2  
(45) Date of Patent: Mar. 10, 2026

(54) PROTEINS WITH CARDIOPROTECTIVE ACTIVITY

(71) Applicant: International Centre for Genetic Engineering and Biotechnology (ICGEB), Trieste (IT)

(72) Inventors: Mauro Giacca, Trieste (IT); Giulia Ruozi, Trieste (IT); Francesca Bortolotti, Trieste (IT)

(73) Assignee: International Centre for Genetic Engineering and Biotechnology (ICGEB), Trieste (IT)

( * ) Notice: Subject to any disclaimer, the term of this patent is extended or adjusted under 35 U.S.C. 154(b) by 733 days.

(21) Appl. No.: 17/606,080

(22) PCT Filed: Apr. 30, 2020

(86) PCT No.: PCT/EP2020/062156  
§ 371 (c)(1),  
(2) Date: Oct. 25, 2021

(87) PCT Pub. No.: WO2020/221906  
PCT Pub. Date: Nov. 5, 2020

(65) Prior Publication Data  
US 2022/0193260 A1     Jun. 23, 2022

(30) Foreign Application Priority Data

Apr. 30, 2019     (GB) .................................... 1906052

(51) Int. Cl.  
*A61K 48/00*        (2006.01)  
*A61K 38/17*        (2006.01)  
*C07K 14/47*        (2006.01)

(52) U.S. Cl.  
CPC ........ *A61K 48/005* (2013.01); *A61K 38/1709* (2013.01); *C07K 14/47* (2013.01); *A01K 2207/20* (2013.01); *A01K 2217/052* (2013.01); *A01K 2227/105* (2013.01); *A01K 2267/0393* (2013.01); *C12N 2750/14143* (2013.01)

(58) Field of Classification Search  
None  
See application file for complete search history.

(56) References Cited

U.S. PATENT DOCUMENTS 7,312,079 B1 * 12/2007 Hu ....................... C12N 9/1048  
                                                                    435/325  
2017/0209621 A1     7/2017 Bhutani et al.

FOREIGN PATENT DOCUMENTS

KR      20190085378 A     7/2019  
RU      2014110508 A     11/2015  
WO      WO-02/08284 A2     1/2002

| WO | WO-2004084800 A2 | 10/2004 | |
|---|---|---|---|
| WO | WO-2008124724 A1 | 10/2008 | |
| WO | WO-2011/100197 A1 | 8/2011 | |
| WO | WO-2011094137 A1 * | 8/2011 | ............. A61K 38/17 |
| WO | WO-2013049674 A1 | 4/2013 | |
| WO | WO-2013093870 A1 | 6/2013 | |
| WO | WO-2014/165452 A1 | 10/2014 | |

OTHER PUBLICATIONS

Reaven (Arterioscler Thromb Vasc Biol.2012;32:1754-1759) (Year: 2012).*  
Pille et al. (Front Cardiovasc Med. Nov. 8, 2023;10:1276321) (Year: 2023).*  
Banerjee et al. (Circ Heart Fail. May 2013;6(3):364-70) (Year: 2013).*  
Ausubel et al., Current Protocols in Molecular Biology, and periodic supplements, Chapters 9, 13, and 16, John Wiley & Sons (1995).  
Ausubel et al., Short Protocols in Molecular Biology, 4th edition, pp. 7-58 to 7-60 (1999).  
Choi et al., AAV hybrid serotypes: improved vectors for gene delivery, Curr. Gene Ther., 5(3):299-310 (2005).  
Coura et al., The state of the art of adeno-associated virus-based vectors in gene therapy, Virol. J., 4:99 (Oct. 16, 2007).  
NCBI Reference Sequence: NM_001143981.1, *Homo sapiens* chordin like 1 (CHRDL1), transcript variant 1, mRNA, May 4, 2019.  
NCBI Reference Sequence: NM_014888.3, *Homo sapiens* FAM3 metabolism regulating signaling molecule C (FAM3C), transcript variant 1, mRNA, Dec. 25, 2022.  
NCBI Reference Sequence: NM_058186.3, *Homo sapiens* family with sequence similarity 3 member B (FAM3B), transcript variant 1, mRNA, May 4, 2019.  
UniProt ID Q9BU40, CRDL1_Human, Chordin-like protein 1 (Jun. 1, 2001-Dec. 14, 2022).  
UniProt ID: Q92520, FAM3C_Human, Protein FAM3C (Feb. 1, 1997-Dec. 14, 2022).  
UnitProt Id P58499, FAM3B_Human, Protein FAM3B (Dec. 19, 2001-Dec. 14, 2022).  
Wu et al., Adeno-associated virus serotypes: vector toolkit for human gene therapy, Mol. Ther., 14(3):316-27 (2006).  
Krainock et al., Epicardial Epithelial-to-Mesenchymal Transition in Heart Development and Disease, J. Clin. Med., 5(2):27 (Feb. 2016).  
Roy et al., Epithelial-to-Mesenchymal Transition Enhances the Cardioprotective Capacity of Human Amniotic Epithelial Cells, Cell Transplant, 24(6):985-1002 (2015).  
Al-Dujaili et al., Relationship Between Chordin Like-1 Protein Level and Patients with Pulmonary Arterial Hypertension Disease, Int. J. Pharm. Quality Assurance, 9(3):308-16 (2018).  
Altschul et al., Basic Local Alignment Search Tool, J. Mol. Biol., 403-410 (1990).  
Ausubel et al., Short Protocols in Molecular Biology, Ch. 18 (1999).  
Bendre et al., Fam3c modulates osteogenic differentiation by down-regulating Runx2, Diffentiation, 93:50-57 (2017).

(Continued)

*Primary Examiner* — Sergio Coffa

(57) ABSTRACT

A protein selected from the group consisting of Chrdl1, Fam3c, Fam3b and a fragment thereof, or a polynucleotide encoding therefor, for use in treating or reducing the risk of heart disease.

40 Claims, 13 Drawing Sheets

Specification includes a Sequence Listing.

(56)            References Cited

OTHER PUBLICATIONS

Bortolotti et al., In Vivo Functional Selection Identifies Cardiotrophin-1 as a Cardiac Engraftment Factor for Mesenchymal Stromal Cells. Circulation 136, 1509-1524 (2017).

Bujak et al., The role of TGF-beta signaling in myocardial infarction and cardiac remodeling. Cardiovasc. Res., 74, 184-195 (2007).

Cai et al., Targeted genome editing by lentiviral protein transduction of zinc-finger and TAL-effector nucleases, Elife, e01911 (2014).

Cardinale et al., Early detection of anthracycline cardiotoxicity and improvement with heart failure therapy, Circulation, 131:1981-8 (2015).

Chandra et al., Neurogenesin-1 differentially inhibits the osteoblastic differentiation by bone morphogenetic proteins in C2C12 cells, Biochem. Biophys. Res. Commun., 344(3):786-91 (2006).

Chen et al., FAM3C activates HSF1 to suppress hepatic gluconeogenesis and attenuate hyperglycemia of type 1 diabetic mice, Oncotarget, 8(62):106038-49 (2017).

Chen et al., Hepatic Activation of the FAM3C-HSF1-CaM Pathway Attenuates Hyperglycemia of Obese Diabetic Mice, Diabetes, 66(5):1185-97 (2017).

Coffinier et al., Neuralin-1 is a novel Chordin-related molecule expressed in the mouse neural plate, Mech. Dev., 100(1):119-22 (2001).

Devereux et al., A comprehensive set of sequence analysis programs for the VAX, Nucleic Acids Res., 12:387 (1984).

Dong et al., Quantitative analysis of the packaging capacity of recombinant adeno-associated virus, Hum. Gene Ther., 7(17):2101-12 (1996).

Dos Santos Coura et al., The state of the art of adeno-associated virus-based vectors in gene therapy, Virol. J., 4:99 (2007).

EBI accession No. GSP:ABB95456 (Database accession No. ABB95456), "Human angiogenesis related protein PRO365 SEQ ID No. 68.", Jun. 15, 2007.

Eulalio et al., Functional screening identifies miRNAs inducing cardiac regeneration, Nature, 492(7429):376-81 (2012).

Gaj et al., Targeted gene knockout by direct delivery of zinc-finger nuclease proteins, Nat. Methods, 9(8):805-7 (2012).

Gavras et al., Angiotensin converting enzyme inhibition in patients with congestive heart failure, Circulation, 58(5):770-6 (1978).

Goldberger, Aldosterone and the Edema of Congestive Heart Failure, Am. J. Cardiol., 15:274 (1965).

Gottlieb et al., Hemodynamic and neurohormonal effects of the angiotensin II antagonist losartan in patients with congestive heart failure, Circulation, 88(4 Pt 1):1602-9 (1993).

Grimmond et al. The mouse secretome: functional classification of the proteins secreted into the extracellular environment. Genome Res., 13, 1350-1359 (2003).

Gustafsson et al., Autophagy in ischemic heart disease, Circ. Res., 104(2):150-8 (2009).

International Application No. PCT/EP2020/062156, International Search Report and Written Opinion, mailed Sep. 1, 2020.

Jhund et al., The neprilysin pathway in heart failure: a review and guide on the use of sacubitril/valsartan, Heart, 102(17):1342-7 (2016).

Kane et al., Chordin-like 1, a bone morphogenetic protein-4 antagonist, is upregulated by hypoxia in human retinal pericytes and plays a role in regulating angiogenesis, Mol. Vis., 14:1138-48 (2008).

Kimura et al., Dissection of the autophagosome maturation process by a novel reporter protein, tandem fluorescent-tagged LC3. Autophagy 3, 452-460 (2007).

Kinch, An overview of FDA-approved biologics medicines, Drug Discov. Today, 20(4):393-8 (2015).

Krijnen, et al. Apoptosis in myocardial ischaemia and infarction. J. Clin. Pathol. 55, 801-811 (2002).

Laflamme et al., Heart regeneration, Nature, 473(7347):326-35 (2011).

Lahsnig et al., ILEI requires oncogenic Ras for the epithelial to mesenchymal transition of hepatocytes and liver carcinoma progression, Oncogene, 28(5):638-50 (2009).

Laughlin et al., Spliced adenovirus-associated virus RNA, Proc. Natl. Acad. Sci. USA, 76(11):5567-71 (1979).

Li et al., Phosphoinositide 3-Kinase Gamma Inhibition Protects From Anthracycline Cardiotoxicity and Reduces Tumor Growth, Circulation, 138(7):696-711 (2018).

Maetzig et al., Retroviral protein transfer: falling apart to make an impact, Gene Ther., 12(5):389-409 (2012).

Mancuso et al., Gene therapy for red-green colour blindness in adult primates, 461(7265):784-7 (2009).

Matsuzaki et al., Efficacy and safety of tolvaptan in heart failure patients with volume overload despite the standard treatment with conventional diuretics: a phase III, randomized, double-blind, placebo-controlled study (Quest study), Cardiovasc. Drugs Ther., 25 Suppl. 1:S33-45 (2011).

Menni et al., Circulating Proteomic Signatures of Chronological Age, J. Gerontol. A Biol. Sci. Med. Sci., 70(7):809-16 (2015).

Mingozzi et al. Induction of immune tolerance to coagulation factor IX antigen by in vivo hepatic gene transfer. J. Clin. Invest., 111, 1347-1356 (2003).

Nakayama et al., A novel chordin-like protein inhibitor for bone morphogenetic proteins expressed preferentially in mesenchymal cell lineages, Dev. Biol., 232(2):372-87 (2001).

O'Connor et al., Effect of nesiritide in patients with acute decompensated heart failure, N. Engl. J. Med., 365(1):32-43 (2011).

Owan et al., Trends in prevalence and outcome of heart failure with preserved ejection fraction, N.Engl. J. Med., 355(3):251-9 (2006).

Pilipenko et al., Genomic organization and expression analysis of the murine Fam3c gene, Gene, 335:159-68 (2004).

Ponikowski et al., 2016 ESC Guidelines for the diagnosis and treatment of acute and chronic heart failure: The Task Force for the diagnosis and treatment of acute and chronic heart failure of the European Society of Cardiology (ESC). Developed with the special contribution of the Heart Failure Association (HFA) of the ESC, Eur. J. Heart Fail, 18(8):891-975 (2016).

Rader, (Re)defining biopharmaceutical, Nat. Biotechnol., 26(7):743-51 (2008).

Robert-Cooperman et al., PANDER KO mice on high-fat diet are glucose intolerant yet resistant to fasting hyperglycemia and hyperinsulinemia, FEBS Lett., 585(9):1345-9 (2011).

Robert-Cooperman et al., Targeted disruption of pancreatic-derived factor (Pander, FAM3B) impairs pancreatic beta-cell function, Diabetes, 59(9):2209-18 (2010).

Ruozi et al., AAV-mediated in vivo functional selection of tissue-protective factors against ischaemia. Nat. Commun., 6: 7388 (2015).

Sakuta et al., Ventroptin: a BMP-4 antagonist expressed in a double-gradient pattern in the retina, Science, 293(5527):111-5 (2001).

Swain et al., Congestive heart failure in patients treated with doxorubicin: a retrospective analysis of three trials, Cancer, 97(11):2869-79 (2003).

Swedberg et al., Prolongation of survival in congestive cardiomyopathy by beta-receptor blockade, Lancet, 1(8131):1374-6 (1979).

Tatusova et al., BLAST 2 Sequences, a new tool for comparing protein and nucleotide sequences, FEMS Microbiol. Lett., 174: 247-250 (1999).

Tatusova et al., Erratum to "BLAST 2 Sequences, A new tool for comparing protein and nucleotide sequences", FEMS Microbiol. Lett, 177: 187-188 (1999).

Tebbe et al., Single-bolus injection of recombinant tissue-type plasminogen activator in acute myocardial infarction, Am. J. Cardiol., 64(8):448-53 (1989).

Teerlink et al., Serelaxin in addition to standard therapy in acute heart failure: rationale and design of the RELAX-AHF-2 study, Eur. J. Heart Fail, 19(6):800-9 (2017).

Thollon et al., Electrophysiological effects of S 16257, a novel sino-atrial node modulator, on rabbit and guinea-pig cardiac preparations: comparison with UL-FS 49, Br. J. Pharmacol., 112(1):37-42 (1994).

Waerner et al., ILEI: a cytokine essential for EMT, tumor formation, and late events in metastasis in epithelial cells, Cancer Cell, 10(3):227-39 (2006).

Wang et al., Efficacy and Safety of 1-Hour Infusion of Recombinant Human Atrial Natriuretic Peptide in Patients With Acute Decompensated

(56)         References Cited

OTHER PUBLICATIONS

Heart Failure: A Phase III, Randomized, Double-Blind, Placebo-Controlled, Multicenter Trial, Medicine (Baltimore), 95(9):e2947 (2016).

Wang et al., Inflammation, Autophagy, and Apoptosis After Myocardial Infarction. J Am Heart Assoc., 7(9):e008024 (2018).

Xin et al., Mending broken hearts: cardiac development as a basis for adult heart regeneration and repair, Nat. Rev. Mol. Cell Biol., 14(8):529-41 (2013).

Yang et al., Mechanisms of glucose-induced secretion of pancreatic-derived factor (PANDER or FAM3B) in pancreatic beta-cells, Diabetes, 54(11):3217-28 (2005).

Yellon et al., Myocardial reperfusion injury, N. Engl. J. Med., 357(11):1121-35 (2007).

Zacchigna et al. Paracrine effect of regulatory T cells promotes cardiomyocyte proliferation during pregnancy and after myocardial infarction. Nature communications 9, 2432 (2018).

Zacchigna et al., Adeno-associated virus vectors as therapeutic and investigational tools in the cardiovascular system. Circ Res 114, 1827-1846 (2014).

Zamorano et al., 2016 ESC Position Paper on cancer treatments and cardiovascular toxicity developed under the auspices of the ESC Committee for Practice Guidelines: The Task Force for cancer treatments and cardiovascular toxicity of the European Society of Cardiology (ESC), Eur. Heart J., 37(36):2768-801 (2016).

Zhang et al., FAM3B mediates high glucose-induced vascular smooth muscle cell proliferation and migration via inhibition of miR-322-5p, Sci. Rep., 7(1):2298 (2017).

Zhu et al., Cloning, expression, and initial characterization of a novel cytokine-like gene family, Genomics, 80(2):144-50 (2002).

International Application No. PCT/EP2020/062156, International Preliminary Report on Patentability, dated Nov. 2, 2021.

Ruozi et al., Cardioprotective factors against myocardial infarction selected in vivo from an AAV secretome library, Sci. Transl. Med., 14(660):eabo0699 (Aug. 2022).

Kaul et al., Thiazolidinedione drugs and cardiovascular risks: a science advisory from the American Heart Association and American College of Cardiology Foundation, Circulation, 121(16):1868-77 (2010).

Li et al., Sulfonylurea use and incident cardiovascular disease among patients with type 2 diabetes: prospective cohort study among women, Diabetes Care, 37(11):3106-13 (2014).

Packer et al., Do DPP-4 Inhibitors Cause Heart Failure Events by Promoting Adrenergically Mediated Cardiotoxicity? Clues From Laboratory Models and Clinical Trials, Circ Res., 122(7):928-32 (2018).

Phung et al., Sulphonylureas and risk of cardiovascular disease: systematic review and meta-analysis, Diabet. Med., 30(10):1160-71 (2013).

Simo et al., Different effects of thiazolidinediones on cardiovascular risk in patients with type 2 diabetes mellitus: pioglitazone versus rosiglitazone, Curr Drug Saf, 5(3):234-44 (2010).

Xia et al., DPP4 inhibitors and cardiovascular outcomes: safety on heart failure, Heart Fail Rev., 22(3):299-304 (2017).

* cited by examiner

FIG. 3A
FIG. 3B
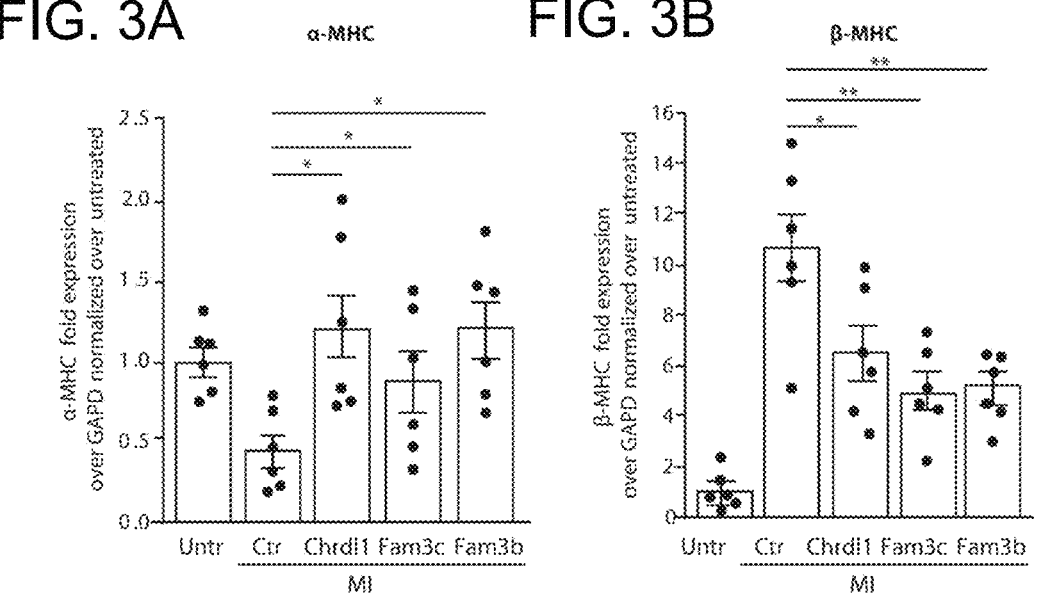
FIG. 3C
FIG. 3D
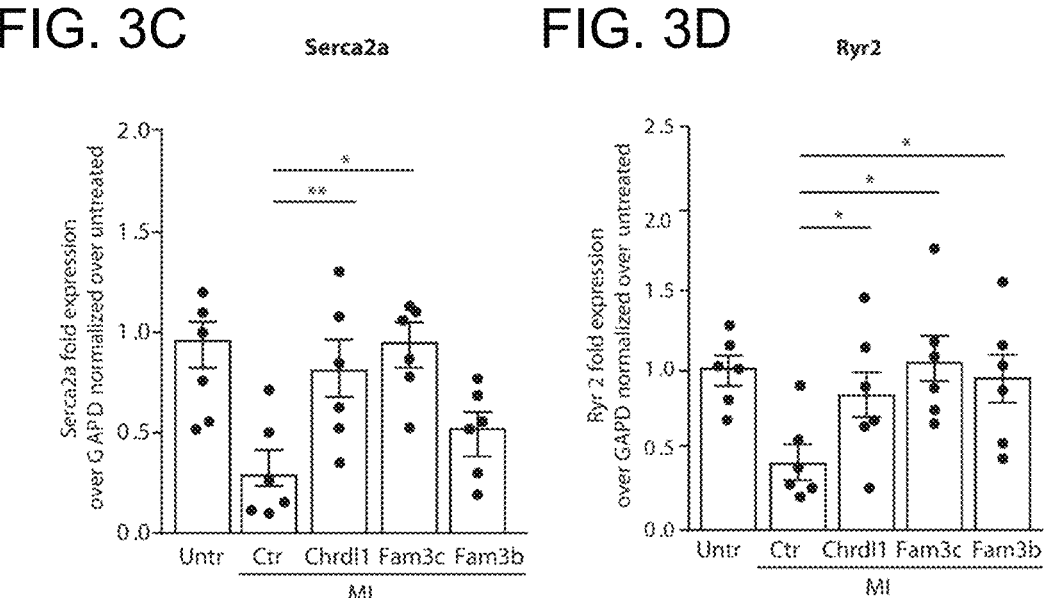

FIG. 4A
FIG. 4B
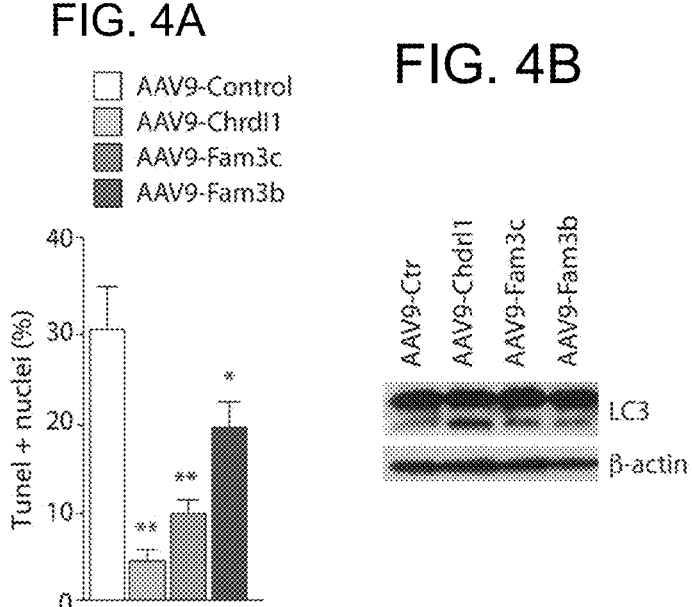
FIG. 4C
FIG. 4D
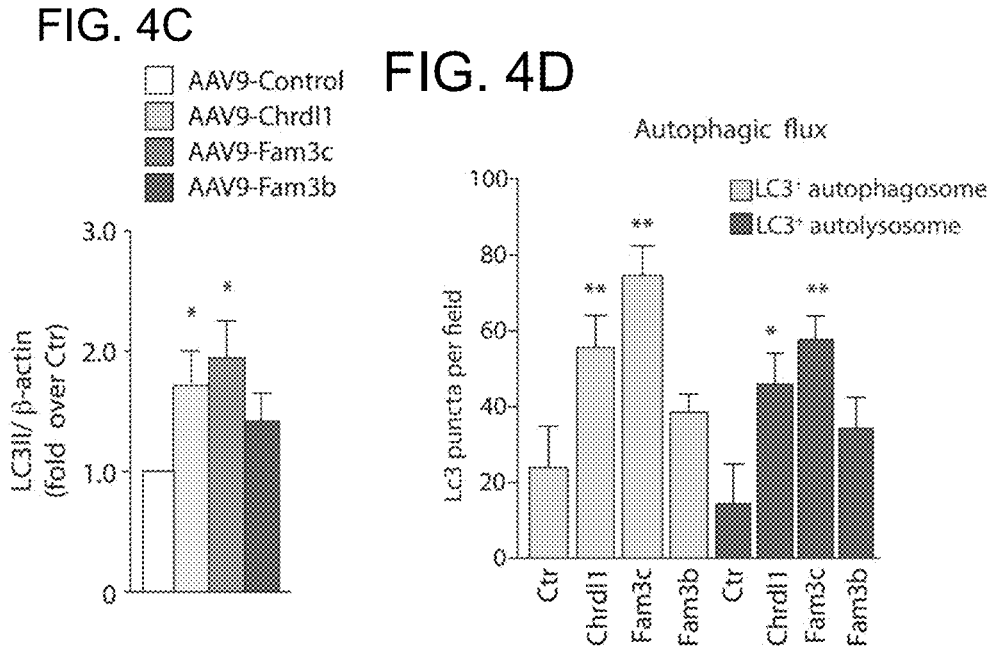

Adult primary cardiac fibroblast

Col1a1

α-SMA

AAV9-Ctr
AAV9-Chrdl1

*Col1a1(l)-Egfp mice 1 months after MI*

PROTEINS WITH CARDIOPROTECTIVE ACTIVITY

CROSS-REFERENCE TO RELATED APPLICATIONS

This application is a U.S. National Phase of International Patent Application No. PCT/EP2020/062156, filed on Apr. 30, 2020, which claims priority to United Kingdom Patent Application No. 1906052.4, filed on Apr. 30, 2019.

INCORPORATION BY REFERENCE OF SEQUENCE LISTING

Incorporated by reference in its entirety is a computer-readable nucleotide/amino acid sequence listing identified as follows: 14, 152 byte ASCII (.txt) file named "56902_Sub-SeqListing.txt"; created on Sep. 19, 2024.

FIELD OF THE INVENTION

The present invention relates to the use of Chrdl1, Fam3c and Fam3b as medicaments, for example in the context of gene therapy or through administration as proteins, such as recombinant or synthetic proteins, for treating or reducing the risk of heart disease. In particular, the invention relates to protection of the heart against the development of heart failure (HF) by preserving cardiac muscle cell viability. Conditions for which the medicaments are effective include, but are not limited to, cardiac ischemia (myocardial infarction and reperfusion injury), cardiac toxic damage and cardiomyopathy of genetic origin.

BACKGROUND OF THE INVENTION

Despite recent advances in cardiovascular surgery and therapy, cardiovascular disorders (CVDs) still account for ~30% of deaths worldwide, of which approximately 50% are due to ischemic heart disease, with a trend to increase to over 23 million by 2030, according to the WHO (www DOT who.int/cardiovascular_diseases/en/). Coronary artery disease and myocardial infarction represents the major cause (65-70% of cases) of heart failure. The prognosis of this condition remains poor, with mortality estimated at 40% of patients at 4 years from diagnosis (Owan, T. E., et al. Trends in prevalence and outcome of heart failure with preserved ejection fraction. N Engl J Med 355, 251-259 (2006)). An essential component underlying the epidemic burden of HF is the inability of the cardiac muscle to undergo regeneration in adult life. Cardiac injury, as a consequence of ischemia, hypertension, infection, inflammation or toxic damage, typically results in irreversible loss of cardiomyocytes (CMs), with consequent fibrosis and scarring (Laflamme, M. A. & Murry, C. E. Heart regeneration. Nature 473, 326-335 (2011); Xin, M., Olson, E. N. & Bassel-Duby, R. Mending broken hearts: cardiac development as a basis for adult heart regeneration and repair. Nat Rev Mol Cell Biol 14, 529-541 (2013)).

Drug development in this area has been marginal in terms of efficacy since the mid 1990s, with all the available drugs being small chemical molecules. If one considers the current ESC guidelines for chronic HF with reduced ejection fraction (Ponikowski, P., et al. 2016 ESC Guidelines for the diagnosis and treatment of acute and chronic heart failure: The Task Force for the diagnosis and treatment of acute and chronic heart failure of the European Society of Cardiology (ESC). Eur J Heart Fail 18, 891-975 (2016)), the three drugs recommended in all patients (ACE inhibitors, β-blockers and mineralocorticoid/aldosterone receptor antagonists) have all been introduced in clinical practice in the 1970s or before (Gavras, H., Faxon, D. P., Berkoben, J., Brunner, H. R. & Ryan, T. J. Angiotensin converting enzyme inhibition in patients with congestive heart failure. Circulation 58, 770-776 (1978); Swedberg, K., Hjalmarson, A., Waagstein, F. & Wallentin, I. Prolongation of survival in congestive cardiomyopathy by beta-receptor blockade. Lancet 1, 1374-1376 (1979); Goldberger, E. Aldosterone and the Edema of Congestive Heart Failure. Am J Cardiol 15, 274 (1965)); of the drugs only recommended in selected patients, angiotensin II receptor blockers-ARBs date back to the mid 1990s (Gottlieb, S. S., et al. Hemodynamic and neurohormonal effects of the angiotensin II antagonist losartan in patients with congestive heart failure. Circulation 88, 1602-1609 (1993)), while the more recent LCZ6969 is based on a combination of an old ARB (valsartan) with sacubitril, belonging to the neprilysin inhibitors class, which were also developed in the late 1980s (Jhund, P. S. & McMurray, J. J. The neprilysin pathway in heart failure: a review and guide on the use of sacubitril/valsartan. Heart 102, 1342-1347 (2016)). The last drug in the recommendations, ivabradin, an $I_f$-channel inhibitor that controls heart rhythm, was also developed in the mid 1990s (Thollon, C., et al. Electrophysiological effects of S 16257, a novel sino-atrial node modulator, on rabbit and guinea-pig cardiac preparations: comparison with UL-FS 49. Br J Pharmacol 112, 37-42 (1994)).

Studies on candidate biological factors for these conditions indicated by biochemical studies (e.g. relaxin, natriuretic peptides, AVP antagonists) have all failed in phase III clinical trials (Teerlink, J. R., et al. Serelaxin in addition to standard therapy in acute heart failure: rationale and design of the RELAX-AHF-2 study. Eur J Heart Fail 19, 800-809 (2017); O'Connor, C. M., et al. Effect of nesiritide in patients with acute decompensated heart failure. N Engl J Med 365, 32-43 (2011); Matsuzaki, M., Hori, M., Izumi, T. & Fukunami, M. Efficacy and safety of tolvaptan in heart failure patients with volume overload despite the standard treatment with conventional diuretics: a phase III, randomized, double-blind, placebo-controlled study (QUEST study). Cardiovasc Drugs Ther 25 Suppl 1, S33-45 (2011); Wang, G., et al. Efficacy and Safety of 1-Hour Infusion of Recombinant Human Atrial Natriuretic Peptide in Patients With Acute Decompensated Heart Failure: A Phase III, Randomized, Double-Blind, Placebo-Controlled, Multicenter Trial. Medicine (Baltimore) 95, e2947 (2016)).

In particular, no drug or treatment of any kind protects the heart during acute ischemia, as well as after myocardial infarction. When a patient undergoes myocardial infarction, cardiac cells progressively die because of the sudden lack of oxygen due to the blockage of a coronary artery. If a patient is revascularized (percutaneous coronary intervention, angioplasty) in the first hours after infarction, a significant portion of the myocardium is spared, however still a large number of myocardial cells irreversibly undergo death. Angioplasty itself promotes additional damage, due to the sudden flux of oxygen occurring after restoring blood perfusion. Due to the incapacity of contractile myocardial cells to undergo significant regeneration in the adult life, the lost portion of the myocardium is irreversibly repaired through formation of a scar, which, in the long term, is a major determinant of heart failure.

Therefore, there is still the strongly felt need to provide a drug, in particular a biological drug mimicking endogenous survival processes, that could save myocardial cells immediately after an insult causing loss of cardiomyocytes and consequent pathological remodeling of the heart. In particular, this need is relevant for the treatment of several conditions leading to HF, including myocardial infarction, reperfusion-injury after angioplasty, cardiac toxic damage by cancer chemotherapy, myocarditis, cardiomyopathy of genetic and non-genetic origin.

Protecting cardiomyocytes from death would be of immense relevance, since it would permit sparing the myocardium and allowing long-term preservation of cardiac integrity and function, avoiding the occurrence of deterioration of cardiac function leading to HF.

Despite the lack of curative therapies, notable progress has been achieved in understanding the cellular and molecular mechanisms leading to tissue degeneration.

Thus, there is also the need for novel biological therapeutics, able to specifically interfere with the different mechanisms of disease onset and progression, offering therapeutic opportunities.

Since the approval of recombinant insulin in 1982 (Humulin®), the number of biotechnological drugs has increased exponentially in the last three decades. If one considers monoclonal antibodies, enzymes, receptor modulators, subunit vaccines and peptides, well over 350 biotechnological drugs have now gained clinical approval and over 400 have entered clinical trials (Kinch, M. S. An overview of FDA-approved biologics medicines. Drug Discov Today 20, 393-398 (2015); Rader, R. A. (Re)defining biopharmaceutical. Nat Biotechnol 26, 743-751 (2008)).

In genetic research, several of the ground-breaking discoveries have been obtained through screening approaches. Starting in the 1980s, gene identification has been initially facilitated by the selection of genomic DNA libraries by hybridization, followed by the identification of cDNAs by antibody screening in phage libraries. In the late 1980s and in the 1990s, functional screening of libraries in cultured cells led to the identification of several oncogenes and cellular receptors for animal viruses. Most early approaches were based on the use of pooled libraries (typically, cDNA libraries), in which a desired factor was identified by phenotype-based selection. In the 2000s, along with advancements in robotics, library screening progressively moved toward high throughput screening (HTS) analysis, based on the use of arrayed libraries. HTS has paved the way to the use not only of cDNA libraries, but also of libraries of peptides, nucleic acids (Eulalio, A., et al. Functional screening identifies miRNAs inducing cardiac regeneration. Nature 492, 376-381 (2012)) and small molecules. Today, the advances in gene transfer permit the field to take a further step forward, namely to screen libraries directly in animals, thus moving from biochemical or phenotypic selection in vitro towards true functional selection in vivo.

SUMMARY OF THE INVENTION

The inventors have utilized a unique procedure based on the in vivo Functional Selection (FunSel) of factors exerting a desired function to identify factors with cardioprotective effects. The inventors' procedure is based on the use of a library of AAV vectors, which are exquisite tools for highly efficient cardiac gene transfer.

Of note, factor identification by FunSel does not require that the selected factors play a role in a given tissue during normal physiology, thus extending the range of potentially therapeutic proteins to all secreted factors encoded by the genome.

The inventors have surprisingly found that the three factors Chrdl1 (Chordin-like protein 1), Fam3c and Fam3b, although exerting completely different biological activities, commonly share cardioprotective effects.

The three novel cardioprotective proteins Chrdl1, Fam3c and Fam3b are highly homologous between mouse and humans (93%, 94% and 79% respectively).

These three factors protect from cardiac cell death induced by ischemia and other kind of damage, including treatment with chemotherapeutic agents.

Accordingly, the present invention relates to the factors Chrdl1, Fam3c and Fam3b for use as medicaments.

In one aspect, the invention provides a protein selected from the group consisting of Chrdl1, Fam3c, Fam3b and fragments thereof, or a polynucleotide encoding therefor, for use in treating or reducing the risk of heart disease.

In another aspect, the invention provides Chrdl1 or a fragment thereof, or a polynucleotide encoding therefor, for use in treating or reducing the risk of heart disease. In another aspect, the invention provides Fam3c or a fragment thereof, or a polynucleotide encoding therefor, for use in treating or reducing the risk of heart disease. In another aspect, the invention provides a Fam3b or a fragment thereof, or a polynucleotide encoding therefor, for use in treating or reducing the risk of heart disease.

In another aspect, the invention provides a method for treating or reducing the risk of heart disease, wherein the method comprises administering a protein selected from the group consisting of Chrdl1, Fam3c, Fam3b and fragments thereof, or a polynucleotide encoding therefor, to a subject in need thereof.

In some embodiments, the use reduces the risk of heart failure. In some embodiments, the risk of heart failure is reduced in a subject suffering from a heart disease. In some embodiments, the risk of heart failure is reduced in a subject at risk of heart disease.

In one aspect, the invention provides a protein selected from the group consisting of Chrdl1, Fam3c, Fam3b and fragments thereof, or a polynucleotide encoding therefor, for use in reducing the risk of heart failure.

In another aspect, the invention provides Chrdl1 or a fragment thereof, or a polynucleotide encoding therefor, for use in reducing the risk of heart failure. In another aspect, the invention provides Fam3c or a fragment thereof, or a polynucleotide encoding therefor, for use in reducing the risk of heart failure. In another aspect, the invention provides a Fam3b or a fragment thereof, or a polynucleotide encoding therefor, for use in reducing the risk of heart failure.

In another aspect, the invention provides a method for reducing the risk of heart failure, wherein the method comprises administering a protein selected from the group consisting of Chrdl1, Fam3c, Fam3b and fragments thereof, or a polynucleotide encoding therefor, to a subject in need thereof.

In some embodiments, the risk of heart failure is reduced in a subject suffering from a heart disease. In some embodiments, the risk of heart failure is reduced in a subject at risk of heart disease.

In another aspect, the invention provides a protein selected from the group consisting of Chrdl1, Fam3c, Fam3b and fragments thereof, or a polynucleotide encoding therefor, for use in preserving cardiac muscle cell viability.

In another aspect, the invention provides Chrdl1 or a fragment thereof, or a polynucleotide encoding therefor, for use in preserving cardiac muscle cell viability. In another aspect, the invention provides Fam3c or a fragment thereof, or a polynucleotide encoding therefor, for use in preserving cardiac muscle cell viability. In another aspect, the invention provides Fam3b or a fragment thereof, or a polynucleotide encoding therefor, for use in preserving cardiac muscle cell viability.

In another aspect, the invention provides a method for preserving cardiac muscle cell viability, wherein the method comprises administering a protein selected from the group consisting of Chrdl1, Fam3c, Fam3b and fragments thereof, or a polynucleotide encoding therefor, to a subject in need thereof.

In some embodiments, cardiac muscle cell viability is preserved in a subject suffering from a heart disease. In some embodiments, cardiac muscle cell viability is preserved in a subject at risk of a heart disease.

An example amino acid sequence of Chrdl1 is SEQ ID NO: 1. An example nucleotide sequence encoding Chrdl1 is SEQ ID NO: 4.

An example amino acid sequence of Fam3c is SEQ ID NO: 2. An example nucleotide sequence encoding Fam3c is SEQ ID NO: 5.

An example amino acid sequence of Fam3b is SEQ ID NO: 3. An example nucleotide sequence encoding Fam3b is SEQ ID NO: 6.

In some embodiments, the protein comprises an amino acid sequence that has at least 70%, 75%, 80%, 85%, 90%, 95%, 96%, 97%, 98% or 99% identity to SEQ ID NO: 1. In some embodiments, the protein comprises an amino acid sequence that has at least 70%, 75%, 80%, 85%, 90%, 95%, 96%, 97%, 98% or 99% identity to SEQ ID NO: 2. In some embodiments, the protein comprises an amino acid sequence that has at least 70%, 75%, 80%, 85%, 90%, 95%, 96%, 97%, 98% or 99% identity to SEQ ID NO: 3.

In some embodiments, the protein comprises the amino acid sequence of SEQ ID NO: 1. In some embodiments, the protein comprises the amino acid sequence of SEQ ID NO: 2. In some embodiments, the protein comprises the amino acid sequence of SEQ ID NO: 3.

In some embodiments, the polynucleotide comprises a nucleotide sequence that has at least 70%, 75%, 80%, 85%, 90%, 95%, 96%, 97%, 98% or 99% identity to SEQ ID NO: 4. In some embodiments, the polynucleotide comprises a nucleotide sequence that has at least 70%, 75%, 80%, 85%, 90%, 95%, 96%, 97%, 98% or 99% identity to SEQ ID NO: 5. In some embodiments, the polynucleotide comprises a nucleotide sequence that has at least 70%, 75%, 80%, 85%, 90%, 95%, 96%, 97%, 98% or 99% identity to SEQ ID NO: 6.

In some embodiments, the polynucleotide comprises the nucleotide sequence of SEQ ID NO: 4. In some embodiments, the polynucleotide comprises the nucleotide sequence of SEQ ID NO: 5. In some embodiments, the polynucleotide comprises the nucleotide sequence of SEQ ID NO: 6.

The heart disease may, for example, be due to loss of cardiomyocytes as a consequence of myocardial infarction, reperfusion-injury after percutaneous coronary intervention (coronary angioplasty), hypertension, cardiac toxic damage (in particular, by cancer chemotherapy), myocarditis, cardiomyopathy of genetic and non-genetic origin.

In some embodiments, the heart disease is associated with cardiac ischemia. In some embodiments, the heart disease is associated with loss of cardiomyocytes.

In some embodiments, the heart disease is selected from myocardial infarction; the consequences of myocardial infarction; reperfusion-injury after percutaneous coronary intervention (coronary angioplasty); myocarditis; hypertension; cardiac toxic damage (in particular, by cancer chemotherapy); or cardiomyopathy.

In some embodiments, the heart disease is ventricular dysfunction.

In some embodiments, the heart is protected from myocardial infarction. In some embodiments, cardiac function is preserved after myocardial infarction or percutaneous coronary intervention (coronary angioplasty). In some embodiments, fibrosis after infarction is reduced.

In some embodiments, the protein or polynucleotide results in heart protection from myocardial infarction and/or other conditions leading to loss of cardiomyocytes, preferably preserving cardiac function and reducing reparative fibrosis.

In some embodiments, heart failure is prevented.

In some embodiments, the protein is administered by direct protein delivery. In some embodiments, the polynucleotide is used in gene therapy.

In some embodiments, the protein is a recombinant protein.

In some embodiments, the protein is obtained from bacterial, yeast or mammalian cell culture. In some embodiments, the protein is obtained from *E. coli, Pichia pastoris* or Chinese Hamster Ovary cells.

In some embodiments, the protein is glycosylated.

In some embodiments, the protein is a fusion protein. In some embodiments, the protein is an Fc fusion protein.

In some embodiments, the polynucleotide is in the form of a vector.

In some embodiments, the polynucleotide is in the form of a viral vector.

In some embodiments, the vector is an adeno-associated viral (AAV) vector, retroviral vector, lentiviral vector or adenoviral vector. In preferred embodiments, the vector is an adeno-associated viral (AAV) vector.

In some embodiments, the vector is an AAV2 vector.

In some embodiments, the vector is an AAV9 vector.

In some embodiments, the vector is an AAV8 vector.

In another aspect, the invention provides a vector for use in treating or reducing the risk of heart disease, wherein the vector comprises a polynucleotide as disclosed herein. In another aspect, the invention provides a vector for use in reducing the risk of heart failure, wherein the vector comprises a polynucleotide as disclosed herein. In another aspect, the invention provides a vector for use in preserving cardiac muscle cell viability, wherein the vector comprises a polynucleotide as disclosed herein.

In some embodiments, the vector is a viral vector.

In some embodiments, the vector is an adeno-associated viral (AAV) vector, retroviral vector, lentiviral vector or adenoviral vector. In preferred embodiments, the vector is an adeno-associated viral (AAV) vector.

In some embodiments, the vector is an AAV2 vector.

In some embodiments, the vector is an AAV9 vector.

In some embodiments, the vector is an AAV8 vector.

In some embodiments, the protein is administered parenterally. In some embodiments, the protein is administered intramyocardially. In some embodiments, the polynucleotide is administered parenterally. In some embodiments, the polynucleotide is administered intramyocardially.

In another aspect, the invention provides a pharmaceutical composition comprising the protein as disclosed herein and a pharmaceutically acceptable vehicle and/or excipient.

In another aspect, the invention provides a pharmaceutical composition comprising the vector as disclosed herein and a pharmaceutically acceptable vehicle and/or excipient.

In some embodiments, the composition is formulated for injection. In preferred embodiments, the composition is formulated for intracardiac or intravenous administration.

In another aspect, the invention provides the pharmaceutical composition disclosed herein for use in treating or reducing the risk of heart disease. In another aspect, the invention provides the pharmaceutical composition disclosed herein for use in reducing the risk of heart failure. In another aspect, the invention provides the pharmaceutical composition disclosed herein for use in preserving cardiac muscle cell viability.

In another aspect, the invention provides a protein selected from the group consisting of Chrdl1, Fam3c, Fam3b and fragments thereof, or a polynucleotide encoding therefor, for use as medicament.

BRIEF DESCRIPTION OF THE DRAWINGS

FIG. 1A. Schematic representation of the pGi vector plasmid used for the Secretome library generation. FIG 1B. Outline of the functional selection (FunSel) procedure to identify cardioactive factors after myocardial infarction (MI). Briefly, Pools of 50 vectors are used to transduce the heart left ventricle; each vector enters a different cardiomyocyte. MI is then induced, which kills most of the cardiomyocytes, however not those that express a cardioprotective factor. After 3 weeks, barcode DNA is recovered from the heart by PCR amplification and frequency of vectors is determined by next generation sequencing (NGS). The number of sequencing reads of vectors with or without infarction are then compared; enriched factors are those that exert cardioprotective activity. FIG. 1C. Cumulative results obtained from the in vivo competitive screening of the 1198 AAV vectors of the library, organized into 24 AAV9-pools, each one composed of 50 inserts of similar size. The frequency of each factor recovered from the heart after infarction (n=9 mice per pool in the MI group) is reported as a ratio to the frequency of the same factor in the absence of the selective treatment (n=6 mice per pool in the Control group), as detected by NGS barcode quantification 3 weeks after AAV pools injection. FIG 1D. Cumulative results obtained from the in vivo screening of the top 200 factors enriched in the first round of selection. From this additional round of selection 3 factors, namely Chrdl1, Fam3c and Fam3b, never associated with cardiac function before, were chosen for further individual investigation. Fold enrichment is expressed as Z-score over undamaged hearts (0=no selection) (Z>1.96 or Z<−1.96; p<0.05).

FIG. 2C. Two months post-MI, mice were sacrificed for histological analysis and scar size was quantified after Masson's trichrome staining (infarct size expressed as % of left ventricle). Heart treatment with the three factors markedly reduced scar size. FIG. 2D. Measurement of CM cross-sectional area after wheat germ agglutinin (WGA) staining of heart sections in AAV2/9-Chrdl1, AAV2/9-Fam3c, AAV2/9-Fam3b or AAV2/9-control treated mice, 60 days after MI.

Treatment with the three factors counteracted post-MI myocardial cell hypertrophy, indicative of improved cardiac function. Data are shown as mean±SEM; * P<0.05;  P<0.01; * P<0.001.

FIGS. 3A-3D. Chrdl1, Fam3c and Fam3b counteract the pattern of gene expression associated with pathological LV remodelling FIG. 3A-3D. Real-time PCR quantification of cardiac expression levels of α-MHC (FIG. 3A), β-MHC (FIG. 3B), SERCA2a (FIG. 3C) and RYR2 (FIG. 3D) genes in non-infarcted animals and in AAV2/9-control or AAV2/9-Chrdl1, AAV2/9-Fam3c or AAV2/9-Fam3b treated hearts 60 days after MI. Values are normalized for GAPDH and expressed as fold over untreated (n=6). Each of the three factors was effective in preserving the heart against pathological LV remodelling. Untr: untreated controls, Ctr: controls with MI. Data are shown as mean±SEM; * P<0.05; ** P<0.01.

FIGS. 4A-4D. AAV9-mediated cardiac overexpression of Chrdl1, Fam3c and Fam3b reduces cell death and promotes beneficial autophagy after MI FIG. 4A. Quantification of apoptosis by the evaluation of TUNEL-positive nuclei (% of total) in the infarct border zone. Animals were transduced with AAV2/9 vectors expressing Chrdl1, Fam3c or Fam3b after MI. TUNEL staining of apoptotic cells was performed 2 days later on frozen heart section (n=5 per group). All three factors were effective at protecting myocardial cells against apoptotic death. An AAV2/9 vector not expressing any proteins was used as a control for these experiments. FIG. 4B-4C. Induction of autophagy was evaluated by analyzing LC3 protein lipidation (conversion from LC3-1 to LC3-11) in the left ventricles of transduced hearts harvested 2 days after MI. Representative western blot (FIG. 4B) and densitometric analysis. Both AAV2/9-Chrdl1 and AAV2/9-Fam3c were capable to induce autophagy (FIG. 4C). FIG. 4D. To analyze the autophagic flux in vivo, adult CD1 mice were transduced with AAV2/9-mRFP-EGFP-LC3 together with AAV2/9s expressing Chrdl1, Fam3c, Fam3b or AAV2/9-Control (n=5 per group). Autophagosomes (yellow) and autolysosomes (red) were quantified 2 days after MI on frozen heart sections by counting yellow and red LC3+ dots. Both AAV2/9-Chrdl1 and AAV2/9-Fam3c markedly increased autophagic flux in vivo. Data are mean±SEM; *P<0.05; **P<0.01.

Figure 5A:
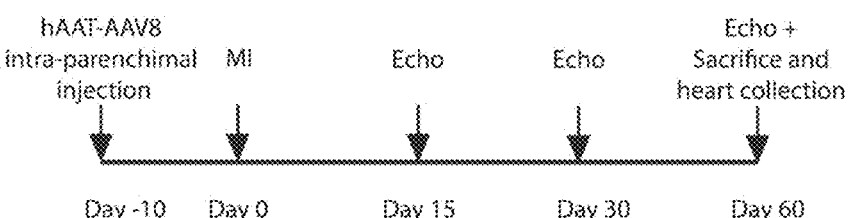
Figure 5B:
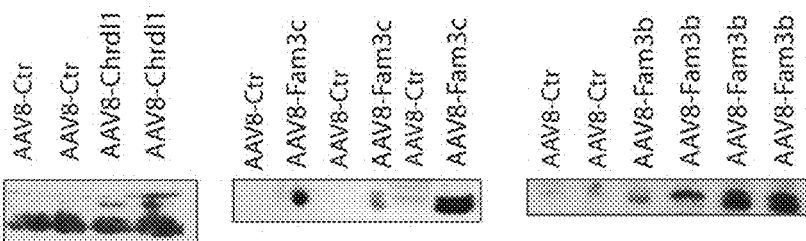
Figure 5C:
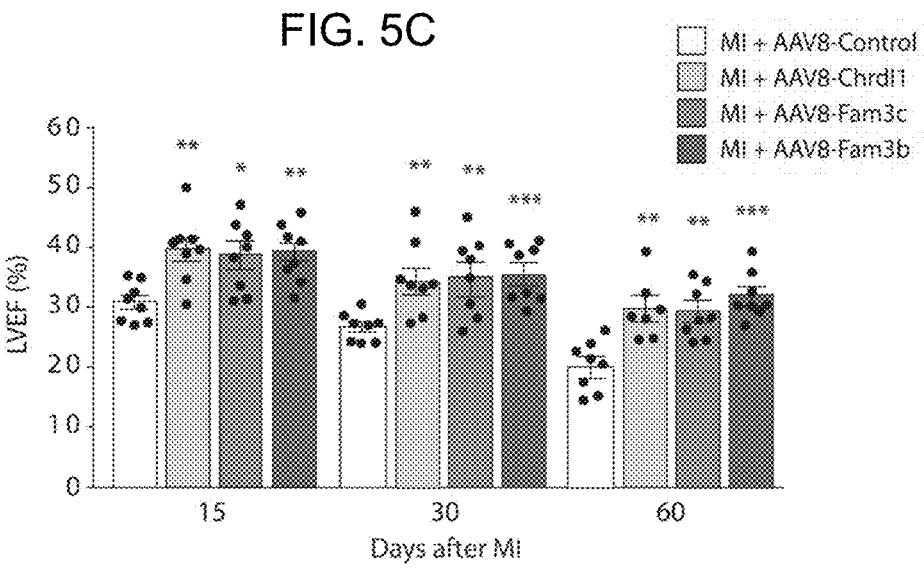
Figures 5D, 5E:
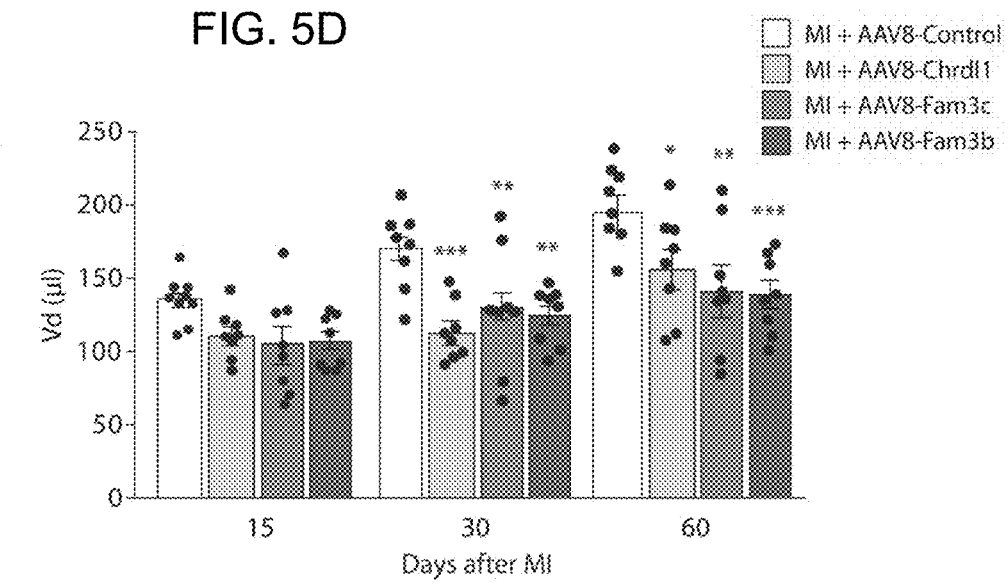

FIGS. 5A-5E. Therapeutic effect of circulating Chrdl1, Fam3c and Fam3b after myocardial infarction FIG. 5A. Outline of the strategy to assess therapeutic efficacy of the factors released into the circulation from the liver, to mimic systemic administration of recombinant proteins. AAV2/8 vectors expressing Chrdl1, Fam3c and Fam3b under the control of the hepatocyte-specific human α-1 antitrypsin (hAAT) promoter were injected into the liver via direct intraparenchimal inoculation (n=7; 3 injection sites per liver for a total of 5×10¹¹ vg/animal); 7 days later the animals underwent MI by coronary artery ligation. FIG. 5B. At 7 days from AAV2/8 intraparenchimal delivery, circulating Chrdl1, Fam3c and Fam3b proteins were detected in animal sera by western blotting. FIG. 5C-5D. At 15, 30 and 60 after MI, circulating Chrld1, Fam3c and Fam3b preserved left ventricular ejection fraction (EF) (FIG. 5C), and reduced cardiac dilation (measured as diastolic volume, μl) (FIG. 5D). FIG. 5E. Scar size was measured as % of LV by Masson's trichrome stain. All three factors reduced infarct size. Data are shown as mean±SEM; *P<0.05; P<0.01; *P<0.001.

Figure 6:
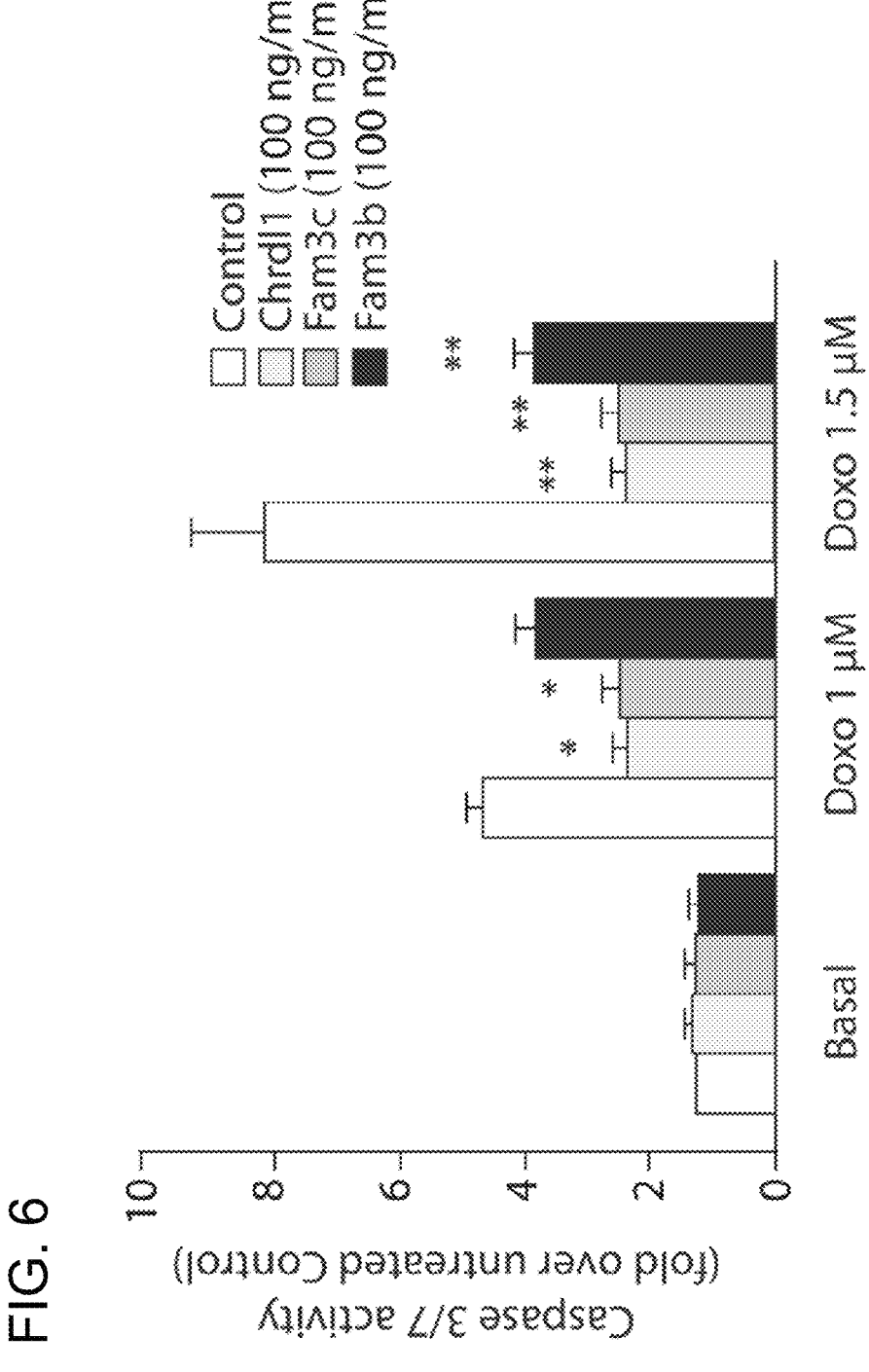

FIG. 6. Recombinant Chrdl1, Fam3c and Fam3b protect cardiomyocytes against doxorubicin-induced cell death Rat cardiomyocytes were treated with the indicated doses of doxorubicin and then administered with 100 ng/ml of the indicated factors. After 20 hours, apoptosis was measured by assessing the levels of caspase 3/7 activation. All three recombinant proteins protected the cells. Data are shown as mean±SEM; *P<0.05; **P<0.01.

Figures 7A, 7B:
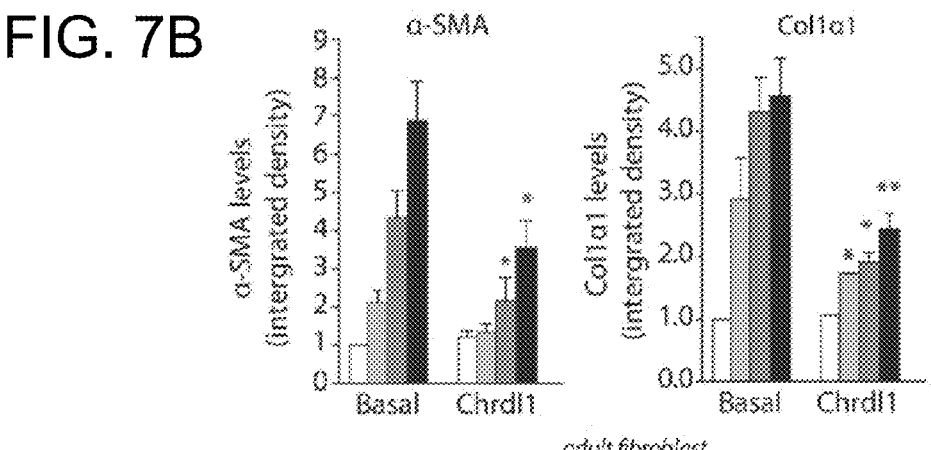
Figure 7C:
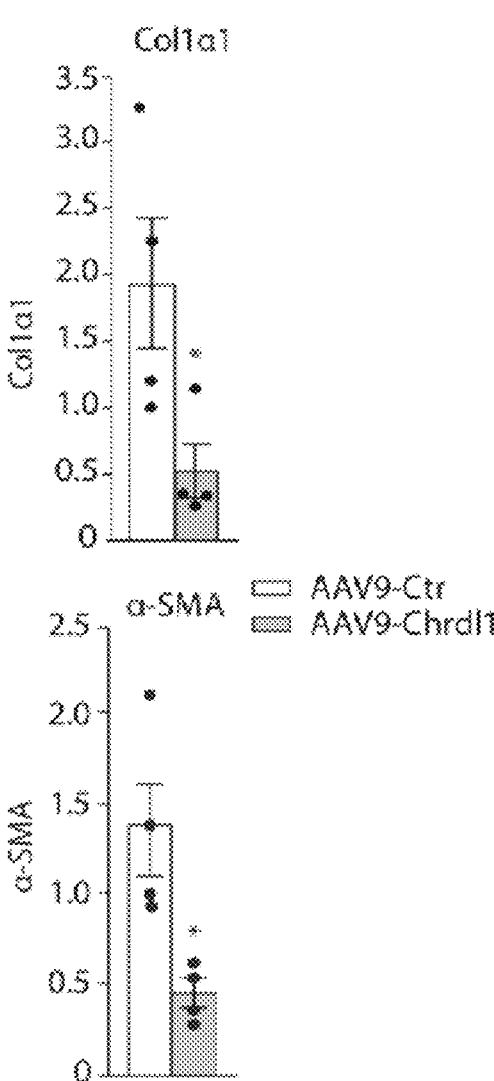
Figure 7D:
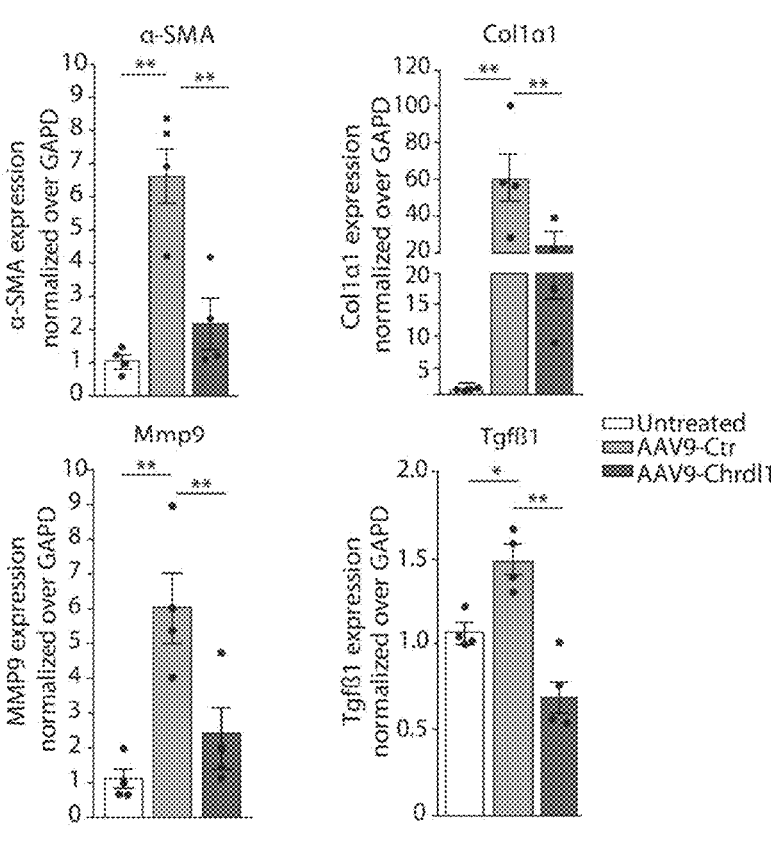

FIGS. 7A-7D. Effect of Chrdl1 in preventing fibroblast activation and cardiac fibrosis after myocardial damage FIG. 7A. Experimental outline to evaluate the effects of Chrdl1 on Tgfβ1-induced conversion of primary adult fibroblasts into pro-fibrotic myofibroblasts. FIG. 7B. Adult fibroblasts were treated with increasing dosages of Tgfβ1 (1-10-50 ng/ml) in the presence or absence of recombinant Chrdl1 (100 ng/ml). Three days after treatments, Col1a1 and α-Sma levels were evaluated by immunofluorescence. FIG. 7C. The modulation of Chrdl1 on the fibrotic response induced by MI was confirmed in vivo in transgenic Col1α1(I)-EGFP mice. AAV2/9-Chrdl1 overexpressing hearts showed a reduction in the fibrotic scar and in the levels of Col1a1 and α-Sma activation. FIG. 7D. Quantification of the transcriptional levels of Col1a1, α-Sma, Tgfβ1 and MMP9 by qPCR in heart tissue of CD1 mice 3 days after MI. Collectively, these results indicate that Chrdl1 exerts an anti-fibrotic effect after MI. Data are shown as mean±SEM; *P<0.05; **P<0.01.

Figures 8A, 8B, 8C:
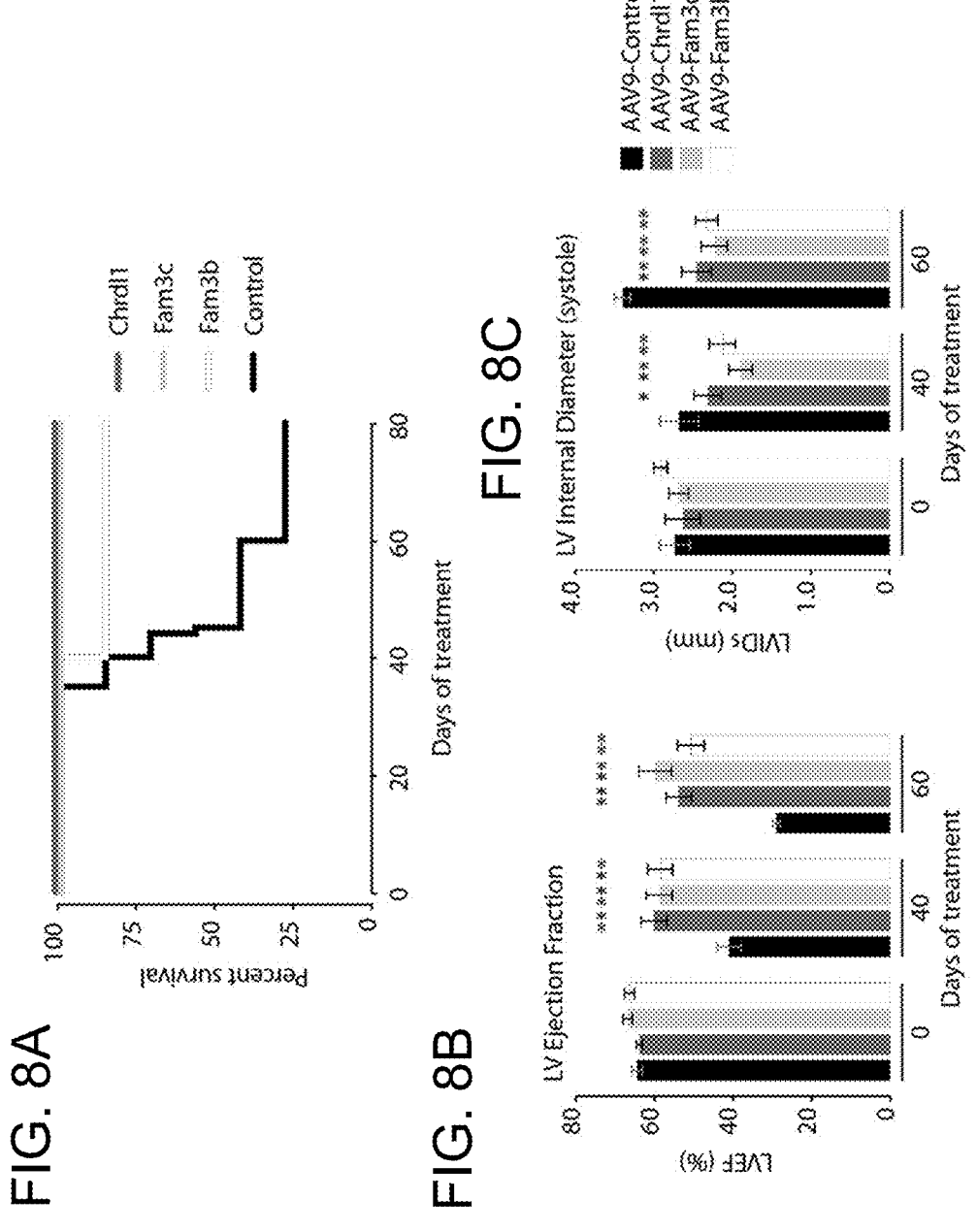

FIGS. 8A-8C. Expression of Chrdl1, Fam3c and Fam3b protects mice from doxorubicin-induced cardiac toxicity and death.

CD1 mice (n=8) were injected intramyocardially with AAV9 vectors expressing the three proteins (Chrdl1, Fam3c or Fam3b), followed by treatment with doxorubicin for 80 days using infusion pumps. FIG. 8A. Kaplan-Meier survival curve showing strong protective activity of the Chrdl1, Fam3c and Fam3b against drug-induced death. FIG. 8B. and FIG. 8C. Left Ventricle (LV) ejection fraction and end-systolic internal diameter, LVEF and LVIDs respectively, at different times during treatment. The data show remarkable cardioprotective effect of treatment with any of the three factors. Data are shown as mean±SEM; *P<0.05; **P<0.01.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Proteins

Chrdl1 is a Bone Morphogenetic Protein (BMP) extracellular inhibitor, mainly expressed in mesenchyme-derived cell types, pericytes in the retina and in neural cells (Sakuta, H., et al. Ventroptin: a BMP-4 antagonist expressed in a double-gradient pattern in the retina. Science 293, 111-115 (2001); Nakayama, N., et al. A novel chordin-like protein inhibitor for bone morphogenetic proteins expressed preferentially in mesenchymal cell lineages. Dev Biol 232, 372-387 (2001); Chandra, A., et al. Neurogenesin-1 differentially inhibits the osteoblastic differentiation by bone morphogenetic proteins in C2C12 cells. Biochem Biophys Res Commun 344, 786-791 (2006); Coffinier, C., Tran, U., Larrain, J. & De Robertis, E. M. Neuralin-1 is a novel Chordin-related molecule expressed in the mouse neural plate. Mech Dev 100, 119-122 (2001)).

The Chrdl1 name derives from its sequence similarity with Chordin, another BMP inhibitor identified as a factor dorsalizing *Xenopus* embryo. Chrdl1 has a spatiotemporal expression pattern distinct from Chordin, but both genes contain cysteine-rich units designed procollagen repeats (CRs), which are also present in a variety of extracellular matrix proteins. CR1 and CR3 are responsible for Chrdl1-BMPs binding. The protein binds with high affinity to BMP4 and with less affinity to BMP5, BMP6 and BMP7.

Fam3b and Fam3c are two members of the family with sequence similarity 3, FAM3 (Zhu, Y., et al. Cloning, expression, and initial characterization of a novel cytokine-like gene family. Genomics 80, 144-150 (2002)). Fam3b, also known as PANDER, is highly expressed in the pancreas, where it participates in regulation of glucose homeostasis and β-cell function (Robert-Cooperman, C. E., Wilson, C. G. & Burkhardt, B. R. PANDER KO mice on high-fat diet are glucose intolerant yet resistant to fasting hyperglycemia and hyperinsulinemia. FEBS Lett 585, 1345-1349 (2011); Robert-Cooperman, C. E., et al. Targeted disruption of pancreatic-derived factor (PANDER, FAM3B) impairs pancreatic beta-cell function. Diabetes 59, 2209-2218 (2010); Yang, J., et al. Mechanisms of glucose-induced secretion of pancreatic-derived factor (PANDER or FAM3B) in pancreatic beta-cells. Diabetes 54, 3217-3228 (2005)).

Fam3c, also known as ILEI, is ubiquitously expressed. It induces inner-ear cell proliferation (Pilipenko, V. V., Reece, A., Choo, D. I. & Greinwald, J. H., Jr. Genomic organization and expression analysis of the murine Fam3c gene. Gene 335, 159-168 (2004)), modulates osteogenic differentiation (Bendre, A., Buki, K. G. & Maatta, J. A. Fam3c modulates osteogenic differentiation by down-regulating Runx2. Differentiation 93, 50-57 (2017)) and has a role in epithelial-mesenchymal transition (EMT) during cancer progression (Waerner, T., et al. ILEI: a cytokine essential for EMT, tumor formation, and late events in metastasis in epithelial cells. Cancer Cell 10, 227-239 (2006); Lahsnig, C., et al. ILEI requires oncogenic Ras for EMT of hepatocytes and liver carcinoma progression. Oncogene 28, 638-650 (2009)). Restoration of its levels in the liver of obese diabetic mice improves insulin resistance and reduces fatty liver (Chen, Z., et al. Hepatic Activation of the FAM3C-HSF1-CaM Pathway Attenuates Hyperglycemia of Obese Diabetic Mice. Diabetes 66, 1185-1197 (2017); Chen, Z., et al. FAM3C activates HSF1 to suppress hepatic gluconeogenesis and attenuate hyperglycemia of type 1 diabetic mice. Oncotarget 8, 106038-106049 (2017)).

An example amino acid sequence of Chrld1 is SEQ ID NO: 1 (human)—UniProt ID: Q9BU40-1.

```
                                        (SEQ ID NO: 1)
MRKKWKMGGMKYIFSLLFFLLLEGGKTEQVKHSETYCMFQDKKYRVGERW

HPYLEPYGLVYCVNCICSENGNVLCSRVRCPNVHCLSPVHIPHLCCPRCP

DSLPPVNNKVTSKSCEYNGTTYQHGELFVAEGLFQNRQPNQCTQCSCSEG

NVYCGLKTCPKLTCAFPVSVPDSCCRVCRGDGELSWEHSDGDIFRQPANR

EARHSYHRSHYDPPPSRQAGGLSRFPGARSHRGALMDSQQASGTIVQIVI

NNKHKHGQVCVSNGKTYSHGESWHPNLRAFGIVECVLCTCNVTKQECKKI

HCPNRYPCKYPQKIDGKCCKVCPGKKAKELPGQSFDNKGYFCGEETMPVY

ESVFMEDGETTRKIALETERPPQVEVHVWTIRKGILQHFHIEKISKRMFE

ELPHFKLVTRTTLSQWKIFTEGEAQISQMCSSRVCRTELEDLVKVLYLER

SEKGHC
```

An example amino acid sequence of Fam3c is SEQ ID NO: 2 (human)—UniProt ID: Q92520-1.

```
                                     (SEQ ID NO: 2)
MRVAGAAKLVVAVAVFLLTFYVISQVFEIKMDASLGNLFARSALDTAARS

TKPPRYKCGISKACPEKHFAFKMASGAANVVGPKICLEDNVLMSGVKNNV

GRGINVALANGKTGEVLDTKYFDMWGGDVAPFIEFLKAIQDGTIVLMGTY

DDGATKLNDEARRLIADLGSTSITNLGFRDNWVFCGGKGIKTKSPFEQHI

KNNKDTNKYEGWPEVVEMEGCIPQKQD
```

An example amino acid sequence of Fam3b is SEQ ID NO: 3 (human)—UniProt ID: P58499-1.

```
                                     (SEQ ID NO: 3)
MRPLAGGLLKVVFVVFASLCAWYSGYLLAELIPDAPLSSAAYSIRSIGER

PVLKAPVPKRQKCDHWTPCPSDTYAYRLLSGGGRSKYAKICFEDNLLMGE

QLGNVARGINIAIVNYVTGNVTATRCEDMYEGDNSGPMTKFIQSAAPKSL

LFMVTYDDGSTRLNNDAKNAIEALGSKEIRNMKERSSWVFIAAKGLELPS

EIQREKINHSDAKNNRYSGWPAEIQIEGCIPKERS
```

Fam3b of SEQ ID NO: 3 (UniProt ID: P58499-1) without the signal peptide, is set forth in SEQ ID NO: 7:

```
                                     (SEQ ID NO: 7)
ELIPDAPLSSAAYSIRSIGERPVLKAPVPKRQKCDHWTPCPSDTYAYRL

LSGGGRSKYAKICFEDNLLMGEQLGNVARGINIAIVNYVTGNVTATRCF

DMYEGDNSGPMTKFIQSAAPKSLLFMVTYDDGSTRLNNDAKNAIEALGS

KEIRNMKFRSSWVFIAAKGLELPSEIQREKINHSDAKNNRYSGWPAEIQ

IEGCIPKERS
```

An example nucleotide sequence encoding Chrld1 (human) is SEQ ID NO: 4 (Chrld1)—Seq ID: NM_001143981.1 (coding sequence).

```
                                     (SEQ ID NO: 4)
ATGAGAAAAAAGTGGAAAATGGGAGGCATGAAATACATCTTTTCGTTGTT

GTTCTTTCTTTTGCTAGAAGGAGGCAAAACAGAGCAAGTAAAACATTCAG

AGACATATTGCATGTTTCAAGACAAGAAGTACAGAGTGGGTGAGAGATGG

CATCCTTACCTGGAACCTTATGGGTTGGTTTACTGCGTGAACTGCATCTG

CTCAGAGAATGGGAATGTGCTTTGCAGCCGAGTCAGATGTCCAAATGTTC

ATTGCCTTTCTCCTGTGCATATTCCTCATCTGTGCTGCCCTCGCTGCCCA

GAAGACTCCTTACCCCCAGTGAACAATAAGGTGACCAGCAAGTCTTGCGA

GTACAATGGGACAACTTACCAACATGGAGAGCTGTTCGTAGCTGAAGGGC

TCTTTCAGAATCGGCAACCCAATCAATGCACCCAGTGCAGCTGTTCGGAG

GGAAACGTGTATTGTGGTCTCAAGACTTGCCCCAAATTAACCTGTGCCTT

CCCAGTCTCTGTTCCAGATTCCTGCTGCCGGGTATGCAGAGGAGATGGAG

AACTGTCATGGGAACATTCTGATGGTGATATCTTCCGGCAACCTGCCAAC

AGAGAAGCAAGACATTCTTACCACCGCTCTCACTATGATCCTCCACCAAG

CCGACAGGCTGGAGGTCTGTCCCGCTTTCCTGGGGCCAGAAGTCACCGGG
```

```
GAGCTCTTATGGATTCCCAGCAAGCATCAGGAACCATTGTGCAAATTGTC

ATCAATAACAAACACAAGCATGGACAAGTGTGTGTTCCAATGGAAAGAC

CTATTCTCATGGCGAGTCCTGGCACCCAAACCTCCGGGCATTTGGCATTG

TGGAGTGTGTGCTATGTACTTGTAATGTCACCAAGCAAGAGTGTAAGAAA

ATCCACTGCCCCAATCGATACCCCTGCAAGTATCCTCAAAAAATAGACGG

AAAATGCTGCAAGGTGTGTCCAGGTAAAAAAGCAAAAGAAGAACTTCCAG

GCCAAAGCTTTGACAATAAAGGCTACTTCTGCGGGGAAGAAACGATGCCT

GTGTATGAGTCTGTATTCATGGAGGATGGGGAGACAACCAGAAAAATAGC

ACTGGAGACTGAGAGACCACCTCAGGTAGAGGTCCACGTTTGGACTATTC

GAAAGGGCATTCTCCAGCACTTCCATATTGAGAAGATCTCCAAGAGGATG

TTTGAGGAGCTTCCTCACTTCAAGCTGGTGACCAGAACAACCCTGAGCCA

GTGGAAGATCTTCACCGAAGGAGAAGCTCAGATCAGCCAGATGTGTTCAA

GTCGTGTATGCAGAACAGAGCTTGAAGATTTAGTCAAGGTTTTGTACCTG

GAGAGATCTGAAAAGGGCCACTGTTAG
```

An example nucleotide sequence encoding Fam3c is SEQ ID NO: 5 (Fam3c)—Seq ID: NM_014888.3 (coding sequence).

```
                                     (SEQ ID NO: 5)
ATGAGGGTAGCAGGTGCTGCAAAGTTGGTGGTAGCTGTGGCAGTGTTTTT

ACTGACATTTTATGTTATTTCTCAAGTATTTGAAATAAAAATGGATGCAA

GTTTAGGAAATCTATTTGCAAGATCAGCATTGGACACAGCTGCACGTTCT

ACAAAGCCTCCCAGATATAAGTGTGGGATCTCAAAAGCTTGCCCTGAGAA

GCATTTTGCTTTTAAAATGGCAAGTGGAGCAGCCAACGTGGTGGGACCCA

AAATCTGCCTGGAAGATAATGTTTTAATGAGTGGTGTTAAGAATAATGTT

GGAAGAGGGATCAATGTTGCCTTGGCAAATGGAAAAACAGGAGAAGTATT

AGACACTAAATATTTTGACATGTGGGGAGGAGATGTGGCACCCATTTATTG

AGTTTCTGAAGGCCATACAAGATGGAACAATAGTTTTAATGGGAACATAC

GATGATGGAGCAACCAAACTCAATGATGAGGCACGGCGGCTCATTGCTGA

TTTGGGGAGCACATCTATTACTAATCTTGGTTTTAGAGACAACTGGGTCT

TCTGTGGTGGGAAGGGCATTAAGACAAAAAGCCCTTTTGAACAGCACATA

AAGAACAATAAGGATACAAACAAATATGAAGGATGGCCTGAAGTTGTAGA

AATGGAAGGATGCATCCCCCAGAAGCAAGACTAA
```

An example nucleotide sequence encoding Fam3b is SEQ ID NO: 6 (Fam3b)—Seq ID: NM_058186.3 (coding sequence).

```
                                     (SEQ ID NO: 6)
ATGCGCCCATTGGCTGGTGGCCTGCTCAAGGTGGTGTTCGTGGTCTTCGC

CTCCTTGTGTGCCTGGTATTCGGGGTACCTGCTCGCAGAGCTCATTCCAG

ATGCACCCCTGTCCAGTGCTGCCTATAGCATCCGCAGCATCGGGGAGAGG

CCTGTCCTCAAAGCTCCAGTCCCCAAAAGGCAAAAATGTGACCACTGGAC

TCCCTGCCCATCTGACACCTATGCCTACAGGTTACTCAGCGGAGGTGGCA

GAAGCAAGTACGCCAAAATCTGCTTTGAGGATAACCTACTTATGGGAGAA
```

-continued

```
CAGCTGGGAAATGTTGCCAGAGGAATAAACATTGCCATTGTCAACTATGT

AACTGGGAATGTGACAGCAACACGATGTTTTGATATGTATGAAGGTGATA

ACTCTGGACCGATGACAAAGTTTATTCAGAGTGCTGCTCCAAAATCCCTG

CTCTTCATGGTGACCTATGACGACGGAAGCACAAGACTGAATAACGATGC

CAAGAATGCCATAGAAGCACTTGGAAGTAAAGAAATCAGGAACATGAAAT

TCAGGTCTAGCTGGGTATTTATTGCAGCAAAAGGCTTGGAACTCCCTTCC

GAAATTCAGAGAGAAAAGATCAACCACTCTGATGCTAAGAACAACAGATA

TTCTGGCTGGCCTGCAGAGATCCAGATAGAAGGCTGCATACCCAAAGAAC

GAAGCTGA
```

Any other polynucleotide coding for the above proteins is comprised in the present invention.

Activity of the proteins of the disclosure and fragments thereof can be readily determined by the skilled person. For example, suitable in vitro assays include: (a) protection from hydrogen peroxide- or doxorubicin-induced cell death, for example using TUNEL assays or Caspase activation assays; (b) induction of autophagy, for example the assaying the formation of LC3-positive autophagy vesicles; and/or (c) for Chrdl1: reduction of BMP and TGFbeta activities, for example activation of aSMA expression in cardiac fibroblasts upon treatment with recombinant TGFbeta, or reduction of SMAD 1/5/8 phosphorylation upon treatment with recombinant BMP4.

The present inventors have surprisingly discovered a previously unknown role of Chrdl1, Fam3c and Fam3b in promoting cardiomyocyte survival, which indicates their therapeutic activity to counteract ischemia and other forms of cardiac damage and thus prevent heart failure.

According to the present invention, Chrdl1, Fam3c and Fam3b effectively increase cardiac function and reduce infarct size after intracardiac injection of viral vectors expressing these factors.

While the present inventors do not wish to be bound to theory or mechanism of action, it is believed that the proteins Chrdl1, Fam3c and Fam3b exert therapeutic effects in the heart by preventing cardiomyocyte apoptosis and inducing cardiomyocytes autophagy. Together, this results in prevention of cardiac function, reduction of fibrosis and left ventricle pathological remodelling and induction of a beneficial expression pattern of genes associated with pathological cardiac remodeling, such as increase in Serca2a (Sarcoplasmic/endoplasmic reticulum calcium ATPase 2a) and RYR2 (Ryanodin receptor 2) and preserved α-myosin-heavy-chain (αMHC) to β-myosin-heavy-chain (βMHC) ratio.

A mechanism through which Chrdl1, Fam3c and Fam3b exert cardioprotective effects on ischemic heart is the preservation of myocytes viability by preventing apoptotic cell death, for example after intracardiac injection of viral vectors expressing the factors.

Chrdl1 and Fam3c may promote beneficial autophagy to counteract cardiomyocytes cell death after myocardial infarction.

Chrdl1, Fam3c and Fam3b may preserve myocyte viability by preventing apoptotic cell death after doxorubicin treatment.

An additional positive effect of Chrdl1 is to prevent cardiac fibroblast activation and cardiac fibrosis.

The heart is an organ that is incapable of significant regeneration during the adult life, thus integrity of cardiac myocytes is maintained by autophagy, a mechanism that permits renewal of specific intracellular components, including mitochondria. This mechanism is of particular relevance after myocardial infarction, since sudden ischemia, or ischemia followed by reperfusion as after percutaneous revascularization, causes significant damage to mitochondria, which start using oxygen to generate damaging chemical species (Yelton, D M., Hausenloy D J. Myocardial reperfusion injury. N. Engl. J. Med. 357, 1121-1135 (2007); Gustafsson A B., Gottlieb R A. Circ. Res. 104(2), 150-158 (2009)). Therefore, autophagy and apoptosis are highly interconnected, with the former mechanism becoming activated after insults to remove damaged cellular organelles as a protective response to avoid apoptotic cell death.

The Chrdl1, Fam3c and Fam3b may therefore be used for cardioprotection, thus reducing the risk of heart disease or heart failure. The cardioprotection may be by preserving cardiac muscle cell viability.

Protein Delivery

As an alternative to the delivery of polynucleotides, the proteins of the invention may be delivered by direct protein delivery.

Proteins may be administered directly to a subject. Is some embodiments, the protein is a fusion protein, preferably a fusion with a second protein capable of increasing the lifespan of the protein in the subject. For example, the protein may be an immunoglobulin Fc domain-fusion protein.

Protein delivery may be via vector delivery (Cai, Y. et al. (2014) Elife 3: e01911; Maetzig, T. et al. (2012) Curr. Gene Ther. 12: 389-409). Vector delivery involves the engineering of viral particles (e.g. lentiviral particles) to comprise the proteins to be delivered to a cell. Accordingly, when the engineered viral particles enter a cell as part of their natural life cycle, the proteins comprised in the particles are carried into the cell.

Protein delivery (Gaj, T. et al. (2012) Nat. Methods 9: 805-7) may also be achieved, for example, by utilising a vehicle (e.g. liposomes).

Polynucleotide

Polynucleotides of the invention may comprise DNA or RNA, preferably DNA. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The nucleotide sequences of the invention disclosed herein may comprise or lack stop codons at their 3' end, for example depending on their position in a bicistronic vector. Thus, the present disclosure encompasses the SEQ ID NOs disclosed herein with the stop codons present or absent.

The polynucleotides may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

Vectors

A vector is a tool that allows or facilitates the transfer of an entity from one environment to another.

In one aspect, the invention provides a vector comprising a polynucleotide of the invention. In preferred embodiments, the vector is a viral vector. In some embodiments, the vector is an adeno-associated viral (AAV) vector, retroviral vector, lentiviral vector or adenoviral vector, preferably an AAV vector.

Adeno-Associated Viral (AAV) Vectors

In one aspect, the invention provides an AAV vector comprising a polynucleotide of the invention.

Preferably, the AAV vector is in the form of an AAV vector particle.

In some embodiments, the AAV vector particle comprises an AAV2 genome. In some embodiments, the AAV vector particle comprises an AAV9 genome. In some embodiments, the AAV vector particle comprises an AAV8 genome.

In some embodiments, the AAV vector particle comprises AAV9 capsid proteins. In some embodiments, the AAV vector particle comprises AAV8 capsid proteins.

In some embodiments, the AAV vector particle comprises an AAV2 genome and AAV9 capsid proteins (AAV2/9). In other embodiments, the AAV vector particle comprises an AAV2 genome and AAV8 capsid proteins (AAV2/8).

Methods of preparing and modifying viral vectors and viral vector particles, such as those derived from AAV, are well known in the art.

The AAV vector may comprise an AAV genome or a fragment or derivative thereof.

AAV is known to be capable of packaging genomes up to 5.2 kb in size (Dong, J.-Y. et al. (1996) Human Gene Therapy 7: 2101-2112).

An AAV genome is a polynucleotide sequence, which may encode functions needed for production of an AAV particle. These functions include those operating in the replication and packaging cycle of AAV in a host cell, including encapsidation of the AAV genome into an AAV particle. Naturally occurring AAVs are replication-deficient and rely on the provision of helper functions in trans for completion of a replication and packaging cycle. Accordingly, the AAV genome of the AAV vector of the invention is typically replication-deficient.

The AAV genome may be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype, isolate or clade of AAV. Thus, the AAV genome may be the full genome of a naturally occurring AAV. As is known to the skilled person, AAVs occurring in nature may be classified according to various biological systems.

Commonly, AAVs are referred to in terms of their serotype. A serotype corresponds to a variant subspecies of AAV which, owing to its profile of expression of capsid surface antigens, has a distinctive reactivity which can be used to distinguish it from other variant subspecies. Typically, a virus having a particular AAV serotype does not efficiently cross-react with neutralising antibodies specific for any other AAV serotype.

AAV serotypes include AAV1, AAV2, AAV3, AAV4, AAV5, AAV6, AAV7, AAV8, AAV9, AAV10 and AAV11, and also recombinant serotypes, such as Rec2 and Rec3, recently identified from primate brain. Any of these AAV serotypes may be used in the invention.

In some embodiments, the AAV vector particle is an AAV1, AAV2, AAV3, AAV4, AAV5, AAV6, AAV7, AAV8, AAV9, AAV10, AAV11, Rec2 or Rec3 AAV vector particle.

In some embodiments, the AAV is an AAV1, AAV2, AAV5, AAV7, AAV8 or AAV9 serotype.

In some embodiments, the AAV is an AAV9 or AAV8 serotype.

In some embodiments, the AAV is an AAV9 serotype. In other embodiments, the AAV is an AAV8 serotype.

The capsid protein may be a mutant capsid protein such as disclosed in WO 2008/124724, which is herein incorporated by reference.

In some embodiments, the AAV vector comprises an AAV8 capsid with an Y733F mutation.

Reviews of AAV serotypes may be found in Choi et al. (2005) Curr. Gene Ther. 5: 299-310 and Wu et al. (2006) Molecular Therapy 14: 316-27. The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV may also be referred to in terms of clades or clones. This refers to the phylogenetic relationship of naturally derived AAVs, and typically to a phylogenetic group of AAVs which can be traced back to a common ancestor, and includes all descendants thereof. Additionally, AAVs may be referred to in terms of a specific isolate, i.e. a genetic isolate of a specific AAV found in nature. The term genetic isolate describes a population of AAVs which has undergone limited genetic mixing with other naturally occurring AAVs, thereby defining a recognisably distinct population at a genetic level.

The skilled person can select an appropriate serotype, clade, clone or isolate of AAV for use in the invention on the basis of their common general knowledge. For instance, the AAV5 capsid has been shown to transduce primate cone photoreceptors efficiently as evidenced by the successful correction of an inherited colour vision defect (Mancuso et al. (2009) Nature 461: 784-7).

The AAV serotype determines the tissue specificity of infection (or tropism) of an AAV. Accordingly, preferred AAV serotypes for use in AAVs administered to patients in accordance with the invention are those which have natural tropism for or a high efficiency of infection of target cells within the heart.

Typically, the AAV genome of a naturally derived sero-
type, isolate or clade of AAV comprises at least one inverted
terminal repeat sequence (ITR). An ITR sequence acts in cis
to provide a functional origin of replication and allows for
integration and excision of the vector from the genome of a
cell. In preferred embodiments, one or more ITR sequences
flank the nucleotide sequences encoding the protein of the
invention. The AAV genome typically also comprises pack-
aging genes, such as rep and/or cap genes which encode
packaging functions for an AAV particle. The rep gene
encodes one or more of the proteins Rep78, Rep68, Rep52
and Rep40 or variants thereof. The cap gene encodes one or
more capsid proteins such as VP1, VP2 and VP3 or variants
thereof. These proteins make up the capsid of an AAV
particle. Capsid variants are discussed below.

A promoter will be operably linked to each of the pack-
aging genes. Specific examples of such promoters include
the p5, p19 and p40 promoters (Laughlin et al. (1979) Proc.
Natl. Acad. Sci. USA 76: 5567-5571). For example, the p5
and p19 promoters are generally used to express the rep
gene, while the p40 promoter is generally used to express the
cap gene.

As discussed above, the AAV genome used in the AAV
vector of the invention may therefore be the full genome of
a naturally occurring AAV. For example, a vector comprising
a full AAV genome may be used to prepare an AAV vector
or vector particle in vitro. However, while such a vector may
in principle be administered to patients, this will rarely be
done in practice. Preferably, the AAV genome will be
derivatised for the purpose of administration to patients.
Such derivatisation is standard in the art and the invention
encompasses the use of any known derivative of an AAV
genome, and derivatives which could be generated by apply-
ing techniques known in the art. Derivatisation of the AAV
genome and of the AAV capsid are reviewed in: Coura and
Nardi (2007) Virology Journal 4: 99, and in Choi et al. and
Wu et al., referenced above.

Derivatives of an AAV genome include any truncated or
modified forms of an AAV genome which allow for expres-
sion of a transgene from an AAV vector of the invention in
vivo. Typically, it is possible to truncate the AAV genome
significantly to include minimal viral sequence yet retain the
above function. This is preferred for safety reasons to reduce
the risk of recombination of the vector with wild-type virus,
and also to avoid triggering a cellular immune response by
the presence of viral gene proteins in the target cell.

Typically, a derivative will include at least one inverted
terminal repeat sequence (ITR), preferably more than one
ITR, such as two ITRs or more. One or more of the ITRs
may be derived from AAV genomes having different sero-
types, or may be a chimeric or mutant ITR. A preferred
mutant ITR is one having a deletion of a trs (terminal
resolution site). This deletion allows for continued replica-
tion of the genome to generate a single-stranded genome
which contains both coding and complementary sequences,
i.e. a self-complementary AAV genome. This allows for
bypass of DNA replication in the target cell, and so enables
accelerated transgene expression.

The one or more ITRs will preferably flank the nucleotide
sequence encoding the protein of the invention at either end.
The inclusion of one or more ITRs is preferred to aid
concatamer formation of the vector of the invention in the
nucleus of a host cell, for example following the conversion
of single-stranded vector DNA into double-stranded DNA
by the action of host cell DNA polymerases. The formation
of such episomal concatamers protects the vector construct during the life of the host cell, thereby allowing for pro-
longed expression of the transgene in vivo.

In preferred embodiments, ITR elements will be the only
sequences retained from the native AAV genome in the
derivative. Thus, a derivative will preferably not include the
rep and/or cap genes of the native genome and any other
sequences of the native genome. This is preferred for the
reasons described above, and also to reduce the possibility
of integration of the vector into the host cell genome.
Additionally, reducing the size of the AAV genome allows
for increased flexibility in incorporating other sequence
elements (such as regulatory elements) within the vector in
addition to the transgene.

The following portions could therefore be removed in a
derivative of the invention: one inverted terminal repeat
(ITR) sequence, the replication (rep) and capsid (cap) genes.
However, in some embodiments, derivatives may addition-
ally include one or more rep and/or cap genes or other viral
sequences of an AAV genome. Naturally occurring AAV
integrates with a high frequency at a specific site on human
chromosome 19, and shows a negligible frequency of ran-
dom integration, such that retention of an integrative capac-
ity in the vector may be tolerated in a therapeutic setting.

Where a derivative comprises capsid proteins i.e. VP1,
VP2 and/or VP3, the derivative may be a chimeric, shuffled
or capsid-modified derivative of one or more naturally
occurring AAVs. In particular, the invention encompasses
the provision of capsid protein sequences from different
serotypes, clades, clones, or isolates of AAV within the same
vector (i.e. a pseudotyped vector).

Chimeric, shuffled or capsid-modified derivatives will be
typically selected to provide one or more desired function-
alities for the AAV vector. Thus, these derivatives may
display increased efficiency of gene delivery, decreased
immunogenicity (humoral or cellular), an altered tropism
range and/or improved targeting of a particular cell type
compared to an AAV vector comprising a naturally occur-
ring AAV genome, such as that of AAV2. Increased effi-
ciency of gene delivery may be effected by improved
receptor or co-receptor binding at the cell surface, improved
internalisation, improved trafficking within the cell and into
the nucleus, improved uncoating of the viral particle and
improved conversion of a single-stranded genome to double-
stranded form. Increased efficiency may also relate to an
altered tropism range or targeting of a specific cell popula-
tion, such that the vector dose is not diluted by administra-
tion to tissues where it is not needed.

Chimeric capsid proteins include those generated by
recombination between two or more capsid coding
sequences of naturally occurring AAV serotypes. This may
be performed for example by a marker rescue approach in
which non-infectious capsid sequences of one serotype are
co-transfected with capsid sequences of a different serotype,
and directed selection is used to select for capsid sequences
having desired properties. The capsid sequences of the
different serotypes can be altered by homologous recombi-
nation within the cell to produce novel chimeric capsid
proteins.

Chimeric capsid proteins also include those generated by
engineering of capsid protein sequences to transfer specific
capsid protein domains, surface loops or specific amino acid
residues between two or more capsid proteins, for example
between two or more capsid proteins of different serotypes.

Shuffled or chimeric capsid proteins may also be gener-
ated by DNA shuffling or by error-prone PCR. Hybrid AAV
capsid genes can be created by randomly fragmenting the
sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. The unrelated protein may also be one which assists purification of the viral particle as part of the production process, i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al., referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The AAV vector of the invention may take the form of a nucleotide sequence comprising an AAV genome or derivative thereof and a sequence encoding the protein of the invention.

The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral capsid. The AAV particle also includes chemically modified forms bearing ligands adsorbed to the capsid surface. For example, such ligands may include antibodies for targeting a particular cell surface receptor.

The AAV vector may comprise multiple copies (e.g., 2, 3 etc.) of the nucleotide sequence referred to herein.

In some embodiments, the polynucleotide further comprises one or more AAV ITRs. In preferred embodiments, the polynucleotide further comprises two AAV ITRs. In some embodiments, the polynucleotide comprises an AAV ITR at its 5' end and an AAV ITR at its 3' end. In some embodiments, the AAV ITRs are AAV2, AAV9 or AAV8 ITRs.

Promoters and Regulatory Sequences

The polynucleotide or vector of the invention may also include elements allowing for the expression of the nucleotide sequence encoding the protein of the invention in vitro or in vivo. These may be referred to as expression control sequences. Thus, the polynucleotide or vector typically comprises expression control sequences (e.g. comprising a promoter sequence) operably linked to the nucleotide sequence encoding the protein of the invention.

Any suitable promoter may be used, the selection of which may be readily made by the skilled person. The promoter sequence may be constitutively active (i.e. operational in any host cell background), or alternatively may be active only in a specific host cell environment, thus allowing for targeted expression of the transgene in a particular cell type (e.g. a tissue-specific promoter). The promoter may show inducible expression in response to presence of another factor, for example a factor present in a host cell. In any event, where the vector is administered for therapy, it is preferred that the promoter should be functional in the target cell background.

In preferred embodiments, the promoter is a liver-specific promoter. In preferred embodiments, the promoter is a liver-specific hAAT promoter.

The liver-specific hAAT promoter may confer selective specificity for hepatocytes. When vectors are administered through the portal vein, the inventors have show that each circulating factor, secreted from the liver, can protect the heart after damage.

Suitable promoters include the chicken beta-actin (CBA) promoter, optionally in combination with a cytomegalovirus (CMV) enhancer element. An example promoter for use in the invention is a CAG promoter.

In some embodiments, the promoter is a CMV promoter.

The polynucleotide or vector of the invention may also comprise one or more additional regulatory sequences which may act pre- or post-transcriptionally. The regulatory sequence may be part of the native transgene locus or may be a heterologous regulatory sequence. The polynucleotide or vector of the invention may comprise portions of the 5'-UTR or 3'-UTR from the native transgene transcript.

Regulatory sequences are any sequences which facilitate expression of the transgene, i.e. act to increase expression of a transcript, improve nuclear export of mRNA or enhance its stability. Such regulatory sequences include for example enhancer elements, post-transcriptional regulatory elements and polyadenylation sites.

Suitable enhancers include the WPRE regulatory element. Suitable poly-A signals include the Bovine Growth Hormone poly-A signal.

Additional regulatory sequences may be readily selected by the skilled person.

Method of Administration

A variety of administration routes and techniques may be utilised, among them parenteral techniques such as intravenous, intracardiac and intra-arterial injections, catheterisations and the like. Average quantities of the active agent may vary and in particular should be based upon the recommendations and prescription of a qualified physician.

The protein, polynucleotide or vector of the invention may be administered systemically (for example by peripheral vein infusion) or may be administered locally or regionally.

Preferably, the protein is administered by parenteral route, in particular intravenous, intraarterial or intramyocardial route.

The administration of the polynucleotide encoding the proteins disclosed herein may be achieved by gene therapy, see for example WO 2013/093870.

According to the present invention, Chrdl1, Fam3c and Fam3b are also active when they reach the infarcted heart through the systemic circulation.

Pharmaceutical Compositions and Injected Solutions

The medicaments, for example proteins, polynucleotides or vectors, of the invention may be formulated into pharmaceutical compositions. These compositions may comprise, in addition to the medicament, a pharmaceutically acceptable carrier, diluent, excipient, buffer, stabiliser or other materials well known in the art. Such materials should be non-toxic and should not interfere with the efficacy of the active ingredient. The precise nature of the carrier or other material may be determined by the skilled person according to the route of administration.

According to the administration route chosen, the compositions may be in solid or liquid form, suitable for oral, parenteral, intravenous or intra-arterial administration. The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution, or glycols such as ethylene glycol, propylene glycol or polyethylene glycol may be included. In some cases, a surfactant, such as pluronic acid (PF68) 0.001% may be used.

For injection at the site of affliction, the active ingredient may be in the form of an aqueous solution which is pyrogen-free, and has suitable pH, isotonicity and stability. The skilled person is well able to prepare suitable solutions using, for example, isotonic vehicles such as Sodium Chloride Injection, Ringer's Injection or Lactated Ringer's Injection. Preservatives, stabilisers, buffers, antioxidants and/or other additives may be included as required.

For delayed release, the medicament may be included in a pharmaceutical composition which is formulated for slow release, such as in microcapsules formed from biocompatible polymers or in liposomal carrier systems according to methods known in the art.

Such compositions are well-known in the art, see for example Remington's Pharmaceutical Sciences; last edition, Mack Pub.

Method of Treatment

It is to be appreciated that all references herein to treatment include curative, palliative and prophylactic treatment; although in the context of the invention references to preventing are more commonly associated with prophylactic treatment. Treatment may also include arresting progression in the severity of a disease.

The treatment of mammals, particularly humans, is preferred. However, both human and veterinary treatments are within the scope of the invention.

The administration regime, dosage and posology will be determined by the physician according to his experience, the disease to be treated and the patient's conditions.

The proteins and/or the polynucleotides of the present invention can be administered either singularly or in combination thereof.

The term "combination", or terms "in combination", "used in combination with" or "combined preparation" as used herein may refer to the combined administration of two or more agents simultaneously, sequentially or separately.

The term "simultaneous" as used herein means that the agents are administered concurrently, i.e. at the same time.

The term "sequential" as used herein means that the agents are administered one after the other.

The term "separate" as used herein means that the agents are administered independently of each other but within a time interval that allows the agents to show a combined, preferably synergistic, effect. Thus, administration "separately" may permit one agent to be administered, for example, within 1 minute, 5 minutes or 10 minutes after the other.

Variants, Derivatives, Analogues, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is –12 for a gap and –4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12: 387). Examples of other software that can perform sequence comparisons include, but are not limited to, the BLAST package (see Ausubel et al. (1999) ibid—Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174: 247-50; FEMS Microbiol. Lett. (1999) 177: 187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" of a full length Chrdl1, Fam3c or Fam3b are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

FunSel, an In Vivo Selection Procedure to Identify Novel Cardiac Therapeutics for Myocardial Infarction We recently developed FunSel (1,2), a novel procedure for the in vivo functional identification of novel therapeutic factors against degenerative conditions that here we applied with the aim to identify factors ensuring cardiac protection after myocardial infarction (MI). This is based on the use of adeno-associated virus (AAV) vectors, which are exquisite tools for highly efficient cardiac gene transfer (3).

Figures 1A, 1B:
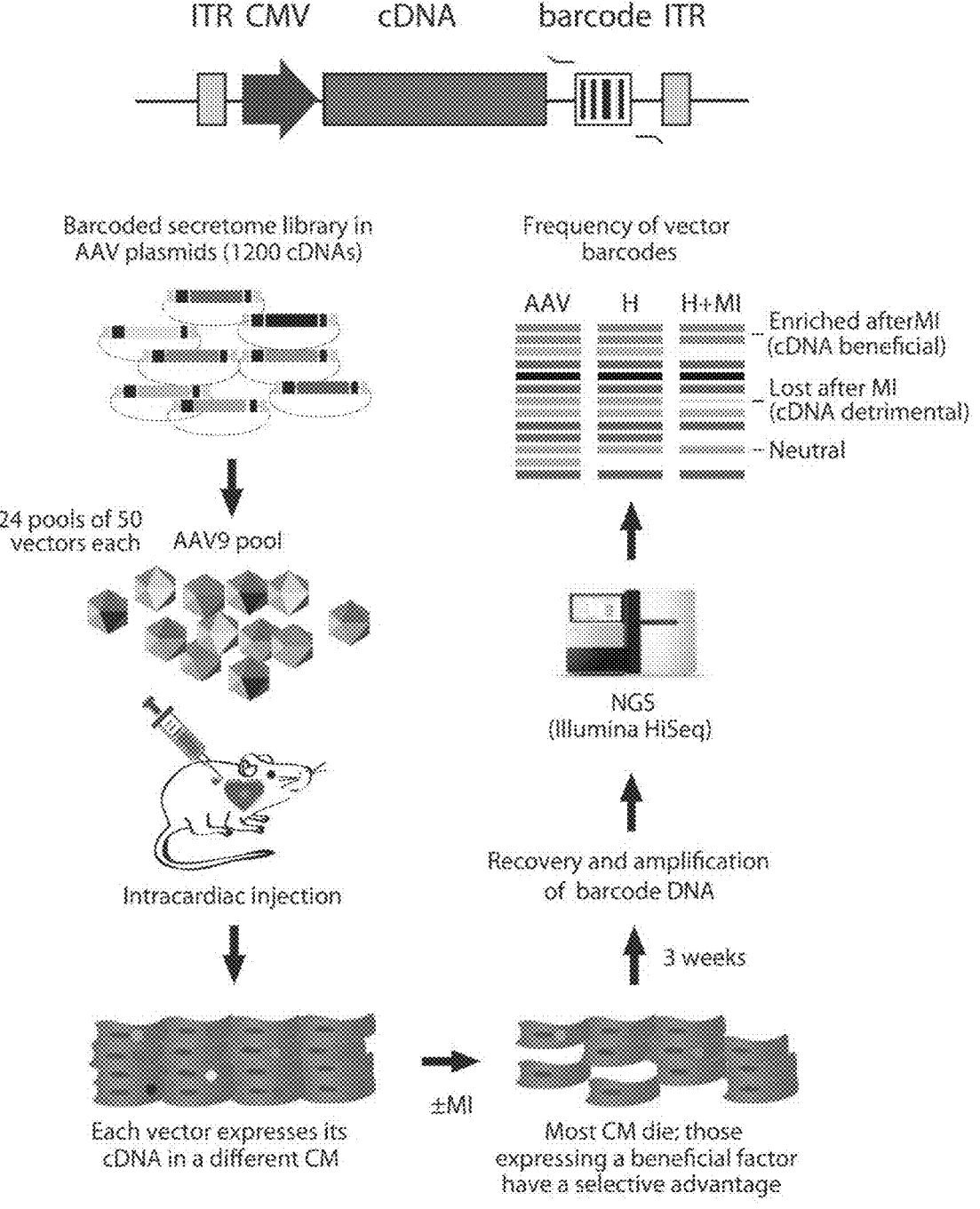
FIGS 1A-1D. 1. FunSel, an in vivo selection procedure to identify novel cardiac therapeutics for myocardial infarction (MI)

In brief, we generated an arrayed library of genes that corresponds to the secretome, defined as the subset of proteins secreted into the extracellular environment of a cell. By a computational approach (4), 2033 unique proteins have been identified in the genome, bearing a signal peptide and lacking any transmembrane domain or intracellular localization signal and thus potentially secreted from the cells. The size of the AAV genome, limiting cloning to 4.5 kb, and the availability of cDNA clones, limited the number of cDNAs suitable for cloning to 1198. The coding region of these genes was individually cloned into a pAAV pGi backbone plasmid under the control of the constitutive CMV IE promoter and confirmed by sequencing. A unique 10-nt barcode, which can be PCR-amplified and sequenced, univocally identifies each clone (FIG. 1A).

FunSel is based on the following strategy: a pool of AAV plasmids from the library, each one coding for a specific factor and being identified by a unique barcode, was used for the batch production of AAV serotype 9 (AAV9) vectors (for a total of 24 pools composed by 50 factors of similar size each). Eight-week-old CD1 mice (n=9 animals for each AAV9 pool), were subjected to myocardial infarction induced by permanent ligation of the left descending coronary artery, which in this setting represents the selective stimulus. Immediately after MI, each AAV9 pool of vectors was injected in vivo into the left ventricle (LV) peri-infarctual region at a multiplicity by which each vector, in principle, enters a different cell ($10^{\wedge 10}$ viral genomes per animal). After three weeks, vector inserts were recovered from the surviving LV tissue and the frequency of each vector was determined by next generation sequencing (NGS) of the barcodes and compared to that found in control animals (n=6 animals per pool) injected with the same AAV9 pool, but not submitted to MI. After infarction most myocyte cells die, however when a cell expresses a protective factor then selectively survives, therefore enrichment for a barcode indicates positive gene selection (beneficial effect), while reduced representation indicates negative selection (neutral or detrimental effect) (Experimental scheme in FIG. 1B).

Figure 1C:
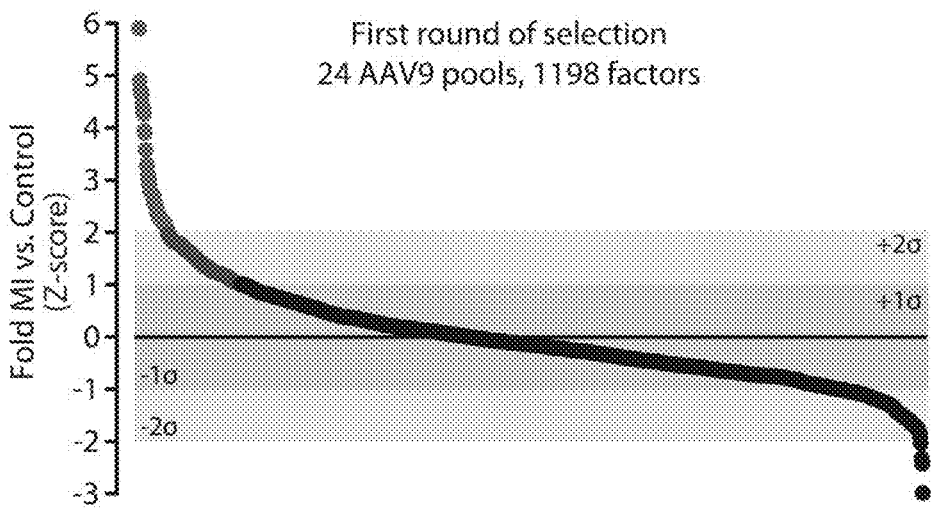
Figure 1D:
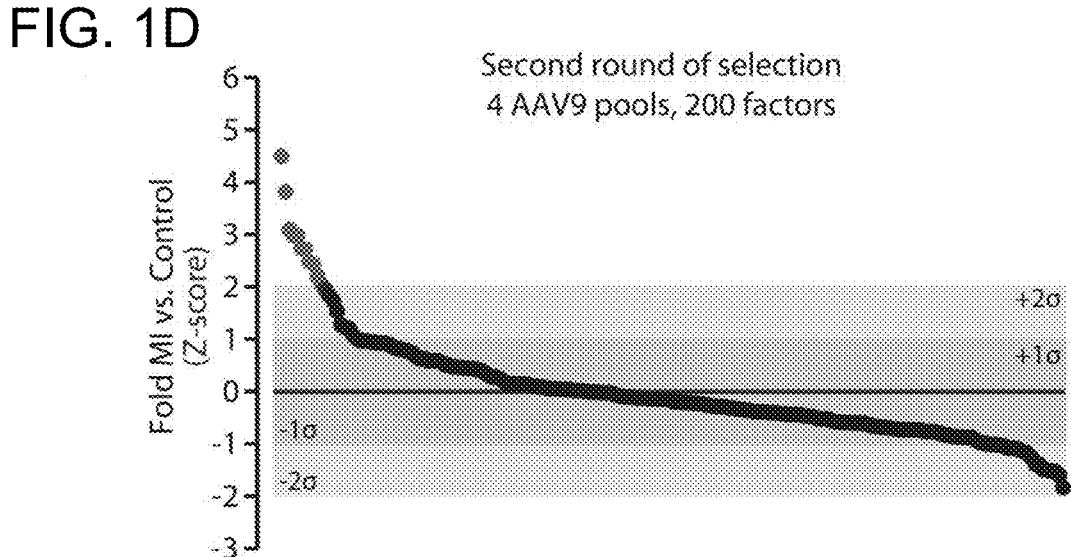

FIG. 1C reports the cumulative results obtained from the in vivo screening of the 1198 factors. In the graph, the frequency of each factor recovered from the heart after MI is reported as a ratio to the frequency of the same factor in the absence of the selective treatment. Based on Z-score calculation, we selected the top 200 performers and run 4 additional screens on these factors (4 pools of 50 vectors). Eleven factors resulted competitively enriched 1.96 Z-score or more (P<0.05) (FIG. 1D). Supporting the robustness of the FunSel approach, among the hits of this second round of screening we found a few known cardioprotective factors and unknown factors somehow related to cardiomyocyte biology. These included Mdk, a pleiotropic molecule, which plays a protective role against cardiac injury and Rln1, a well-described anti-fibrotic agent, able to reduce ROS production, apoptosis and inflammation in the infarcted heart. More notably, however, the top performers included three new proteins for which no information is currently available nor study has been performed relative to cardiac protection. These are Chordin-like 1 (Chrdl1) and two members of the family with sequence similarity 3, namely Fam3b and Fam3c. These factors were chosen for further individual investigation to assess efficacy and mechanism of action.

Example 2

Efficacy of Chrdl1, Fam3c and Fam3b in Preserving Cardiac Integrity and Function after Myocardial Infarction in Mice Based on the FunSel results, we decided to validate and characterize the effect of the selected top secreted factors (Chrdl1, Fam3c and Fam3b) expressed as individual AAV2/9 vectors upon myocardial infarction in mouse hearts, with the specific purpose to assess the capacity of each factor to counteract or reduce ischemic damage and promote cardiac function.

Eight-week-old CD1 mice were subjected to MI and, at the same time, injected in the LV peri-infarcted area with AAV2/9 vectors expressing Chrdl1, Fam3c, Fam3b or a control empty vector ($1 \times 10^{11}$ vg/animal; n=8 per group). Our previous experience indicates that this procedure results in efficient myocardial transduction and month-long expression of the transgene (1,5). Cardiac function of the animals was monitored by echocardiography at 15, 30 and 60 days post MI.

As reported in FIG. 2, AAV2/9-mediated overexpression of Chrdl1, Fam3c or Fam3b successfully preserved LV ejection fraction (LVEF) (FIG. 2A) of infarcted mice when compared to control treated animals. The LVEF values started to be remarkably improved at 15 days post MI and were maintained overtime (60 days after MI: AAV9-Chrdl1 39.96±2.67%, AAV2/9-Fam3c 39.02±2.53% and AAV2/9-Fam3b 32.50±2.70%, compared with 19.86±0.98% for the animals that received the control vector, P<0.001 for all treatments). At both 30 and 60 days post MI, the diastolic LV volume (Vd) was significantly larger, as expected when heart failure starts to occur, in control animals if compared with treated mice (FIG. 2B) (60 days after MI: AAV2/9-Chrdl1 101.22±10.31p1, AAV2/9-Fam3c 107.31±8.85p1 and AAV2/9-Fam3b 115.16±11.03p1, compared with 168.64±7.47p1 for the animals that received the control vector, P<0.001 for all treatments).

Figure 2A:
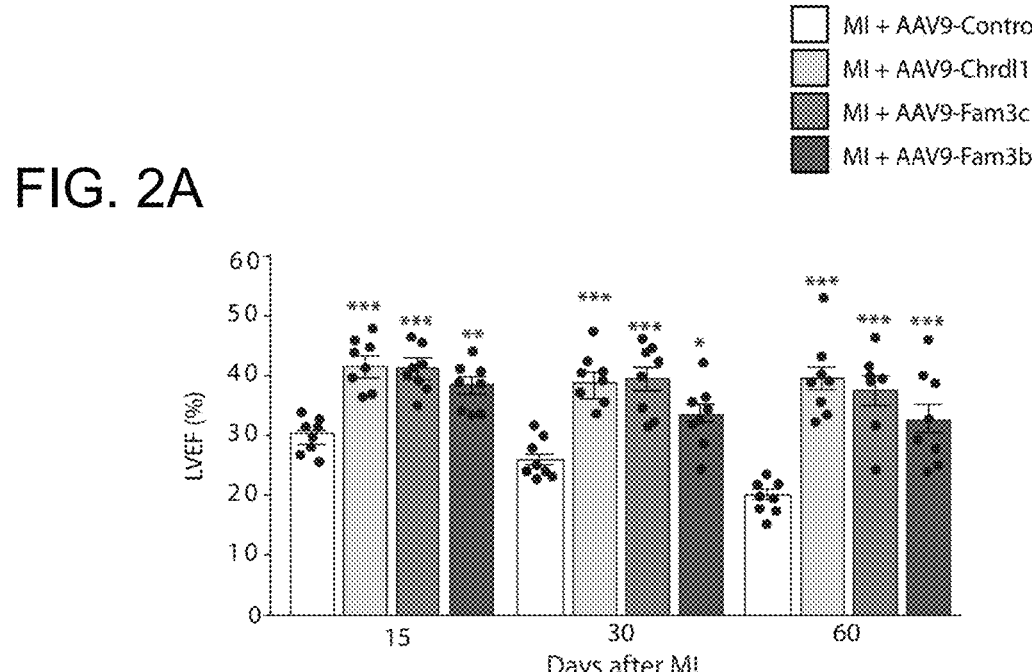
FIGS. 2A-2D. Overexpression of Chrdl1, Fam3c and Fam3b in a mouse model of myocardial infarction FIG 2A-2B. Echocardiographic analysis to evaluate heart function at 15, 30 and 60 days post-MI in adult CD1 mice transduced with AAV2/9-Chrdl1, AAV2/9-Fam3c, AAV2/9-Fam3b or an AAV2/9-control (1×10¹¹ vg/animal; n=8 animals per group). Cardiac overexpression of the three secreted factors mediated by AAV9 vectors preserves left ventricle ejection fraction (LVEF) (FIG. 2A) and reduces cardiac dilation (Vd—left ventricle volume in diastole) (FIG. 2B), if compared with AAV2/9-control animals.
Figure 2B:
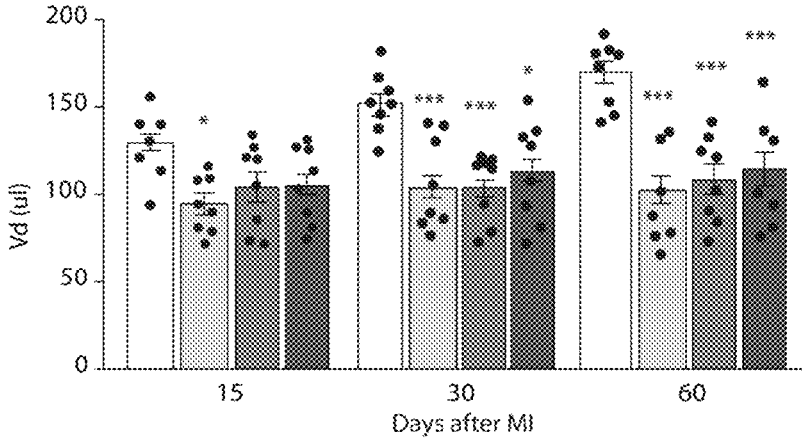
Figure 2C:
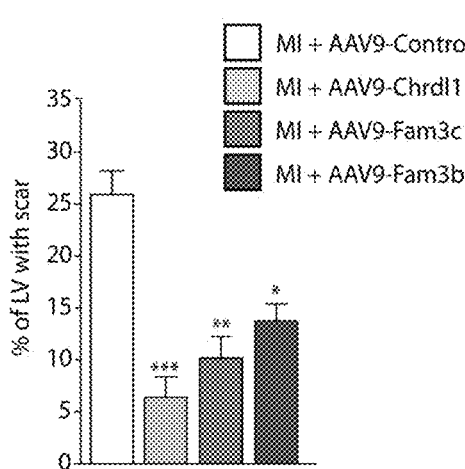

When myocardial infarction occurs, cardiac fibroblasts proliferate, differentiate into myofibroblasts and produce extracellular matrix to create a scar to replace the gap generated by cardiomyocyte loss. This often results in myocardial stiffness and leads to pathological remodelling of the left ventricle, dilatation and dysfunction. Morphometric analysis on trichromic-stained heart sections at day 60 indicated that AAV2/9-Chrdl1, AAV2/9-Fam3c and AAV2/9-Fam3b-treated mice showed significant preservation of LV contractile tissue and reduction of the fibrotic area (infarct size: AAV2/9-Chrdl1 6.88±1.60%, AAV2/9-Fam3c 10.19±2.05%, AAV2/9-Fam3b 13.35±1.79%, versus 26.26±2.35% of the LV in control animals; FIG. 2C).

Figure 2D:
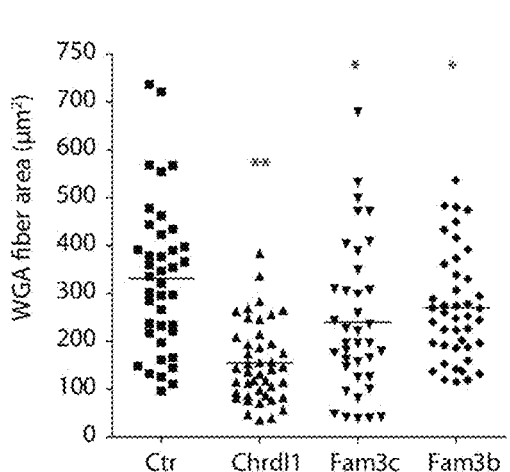

Finally, a wheat germ agglutinin (WGA) staining revealed that no cardiomyocyte hypertrophic response was induced by Chrdl1, Fam3c or Fam3b overexpression, since fibre cross sectional area was not increased in treated animals compared to controls (FIG. 2D).

Taken together, these results indicate that the AAV2/9-mediated cardiac over-expression of Chrdl1, Fam3c or Fam3b after acute ischemia promotes myocyte cell viability, reduces infarct size and preserves cardiac function after myocardial infarction.

Example 3

AAV2/9-Mediated Expression of Chrdl1, Fam3c or Fam3b Counteracts Pathological Left Ventricle Remodelling Associated with the Onset of Heart Failure in Mice Two months after MI, we investigated also the effect of each secreted factor on the expression of a set of genes previously associated with LV pathological remodelling (consisting in overexpression of β-myosin heavy chain (pMHC) and decreased levels of α-myosin heavy chain (αMHC), Sarcoplasmic/endoplasmic reticulum $Ca^{2+}$-AT-Pase 2a (SERCA2a) and ryanodine receptor 2 (RYR2)).

Total RNA was extracted from LV tissue and analysed by qRT-PCR using TaqMan probes specific for the investigated genes. Consistent with echocardiographic and morphometric observations, AAV2/9-Chrdl1, AAV2/9-Fam3c and AAV2/9-Fam3b counteracted the characteristic pattern of gene expression typically associated with pathological LV remodelling observed in AAV2/9-control mice, reducing the level of β-MHC and increasing those of α-MHC, SERCA2a and RYR2 (FIGS. 3A-3D).

Example 4

All Three Factors Preserve Tissue Viability Protecting Cardiomyocytes from Cell Death and Both Chrdl1 and Fam3c Promote Cardiac Beneficial Autophagy after MI So far, the available information on Chrdl1, Fam3c and Fam3b factors is scanty and certainly cannot explain why these factors exert a cardioprotective effect after myocardial infarction. Therefore, we set out to explore possible biological mechanisms that might mediate their activity. Since the FunSel approach is based on factor selection based on cardiomyocyte survival, a first set of experiments was performed by testing the levels of cell death from apoptosis, which is usually massive at two days after coronary artery occlusion (6), in the hearts of infarcted adult CD1 mice treated with the three AAV vectors, compared to controls ($1\times10^{11}$ vg/animal; n=5 per group). Fam3b, Fam3c and, in particular, Chrdl1, were extremely effective in preventing apoptotic cell death in the infarcted hearts, as assessed by nuclear TUNEL (TdT-mediated dUTP nick-end labelling) staining on snap frozen heart section 2 days after MI (% of positive TUNEL nuclei: AAV2/9-Chrdl1 4.01±1.21%, AAV2/9-Fam3c 10.33±1.43%, AAV2/9-Fam3b 19.83±3.01%, versus 30.67±4.38% of in control animals) (quantification in FIG. 4A).

The heart is an organ that is incapable of significant regeneration during the adult life, thus integrity of cardiac myocytes is maintained by autophagy, a mechanism that permits renewal of specific intracellular components, in particular mitochondria. This mechanism is of particular relevance after myocardial infarction, since sudden ischemia, or ischemia followed by reperfusion as after percutaneous revascularization, causes significant damage to mitochondria, which start using oxygen to generate damaging chemical species (7). Not surprising, therefore, autophagy and apoptosis are highly interconnected, with the former mechanism becoming activated after damage to remove damaged cellular organelles as a protective response to avoid apoptotic cell death (8).

To evaluate induction of autophagy after acute cardiac ischemia we injected another group of adult, infarcted CD1 mice with AAV2/9 vectors expressing Chrdl1, Fam3c, Fam3b or a control vector ($1\times10^{11}$ vg/animal; n=5 per treatment). Two days after MI, we found increased conversion of the soluble LC3-1 protein to lipid-bound LC3-11, in particular in the hearts of Chrdl1 and Fam3c treated mice, which associated with the formation of autophagosomes (representative blots and quantification for AAV2/9-Chrdl1, AAV2/9-Fam3c, AAV9-Fam3b and AAV2/9-control hearts in FIGS. 4B and 4C, respectively).

To directly visualize the autophagic flux in the infarcted hearts, we previously generated an AAV2/9 vector expressing the monomeric red fluorescent protein (mRFP)-enhanced green fluorescent protein (EGFP) tandem fluorescent-tagged LC3 protein, derived from the ptfLC3 plasmid, in which green, but not red, fluorescence is sensitive to the pH difference between the neutral autophagosome and the acidic autolysosome (9). This vector was administered, together with AAV2/9-Chrdl1, AAV2/9-Fam3c, AAV2/9-Fam3b or AAV2/9-control ($1\times10^{11}$ vg/animal; n=5 per treatment), immediately after MI. Two days later, the number of yellow, LC3-positive vesicles, and, in particular, of those showing only red fluorescence, was significantly increased in the LV perinfarct region of hearts injected with AAV9-Chrdl1 and Fam3c, indicating that these two factors stimulate the autophagic flux in vivo (quantification of yellow and red puncta for each treatment are reported in FIG. 4D).

Taken together, these results indicate that the AAV2/9-mediated cardiac over-expression of Chrdl1 Fam3c, Fam3b preserves cardiac myocyte viability by preventing apoptotic cell death and, in particular Fam3c and Chrdl1, promoting cardiac beneficial autophagy.

Example 5

Circulating Chrdl1, Fam3c and Fam3b, Produced and Secreted by the Liver Upon AAV8-Mediated Tissue Specific Expression, Counteract Pathological Left Ventricle Remodelling after Myocardial Infarction To assess whether circulating Chrdl1, Fam3b and Fam3c are active once reaching the heart from the circulation, as opposed to being endogenously expressed using viral vectors, we designed a strategy by which each of the three factors is expressed by the liver and secreted into the circulation before myocardial infarction (FIG. 5A). In more detail, we performed an intraparenchimal injection in adult CD1 mice ($5\times10^{11}$ vg/animal; n=6 per group) with AAV vectors serotype 8 (AAV2/8), which selectively transfers genes into liver cells; in these vectors, the factor is expressed under the control of the human α-1 antitrypsin (hAAT) promoter, which ensures specific expression in hepatocytes only (10). Seven days after administration, when the liver was actively producing and releasing dosable amounts of each factor in the circulation (FIG. 5B), myocardial infarction was induced by ligating the left descendant coronary artery.

As reported in FIG. 5C, AAV2/8-mediated liver production of Chrdl1, Fam3c or Fam3b successfully preserved LV ejection fraction (LVEF) of infarcted mice compared to control treated animals. The LVEF values started to be remarkably improved at 15 days post MI and were maintained overtime (60 days after MI: AAV2/8-Chrdl1 28.77±1.66%, AAV2/8-Fam3c 28.09±1.61% and AAV8-

Fam3b 31.22±1.40%, compared to 20.05±1.47% for the animals that received the control vector). Two months after MI, as expected, the diastolic LV volume was significantly larger in control animals compared to treated mice (FIG. 5D) (60 days after MI: AAV2/8-Chrdl1 150.2±10.2 μl, AAV2/8-Fam3c 137.9±16.8 μl and AAV2/8-Fam3b 134.7±9.2 μl, compared to 193.2±11.6 μl for the animals that received the control vector).

Finally, also in this experiment, morphometric analysis on trichromic-stained heart sections at day 60 indicated that AAV8-Chrdl1, AAV2/8-Fam3c and AAV2/8-Fam3b-treated mice showed significant reduction of the fibrotic area (infarct size: AAV2/8-Chrdl1 13.6±3.1%, AAV2/8-Fam3c 15.0±3.4%, AAV2/8-Fam3b 13.2±2.7%, versus 28.7±3.3% of the LV in control animals; FIG. 5E).

Taken together these results prove that each circulating factor, therapeutically expressed from the liver, protect cardiomyocytes from ischemic damage and improve cardiac function after MI. This represents an efficacy test preliminary to the injection of Chrdl1, Fam3c and Fam3b as recombinant proteins.

Example 6

Recombinant Chrdl1, Fam3c and Fam3b Protect Cardiomyocytes Against Doxorubin-Induced Cell Death To evaluate the potential effect of Chrdl1, Fam3c and Fam3b in preserving cell viability upon toxic damage, the corresponding recombinant proteins were tested on primary neonatal rat ventricular cardiomyocytes treated with the chemotherapeutic drug doxorubicin (FIG. 6).

The treatment with 100 ng/ml of Chrdl1, Fam3c or Fam3b recombinant proteins significantly counteracted caspase 3/7 activation (as a measure of apoptotic cell death), after 20 hours of doxorubicin treatment (1 and 1.5 μM).

Example 7

Chrdl1 Prevents Fibroblast Activation and Cardiac Fibrosis after Myocardial Infarction When MI occurs, cardiac fibroblasts proliferate, differentiate into myofibroblasts and stimulate collagen deposition to create a scar to replace the gap generated by cardiomyocyte loss. Of interest, infarcted hearts overexpressing Chrdl1 not only had very small scars but also did not underwent pathological remodelling and dilatation at two months after MI. This was suggestive of a specific effect of Chrdl1 on scar formation, in addition to that on cardiomyocyte survival.

Transforming growth factor-β1 (Tgfβ1), which is expressed at high levels in the scar after MI, is a key inductor of collagen deposition and differentiation of fibroblasts into myofibroblasts (11). To evaluate whether Chrdl1 was able to modulate fibroblast transdifferentiation induced by Tgfβ1, primary adult mouse cardiac fibroblasts were treated for 3 days with different Tgfβ1 dosages (1-10-50 ng/ml) in the presence or absence of recombinant Chrdl1 (100 ng/ml) (FIG. 7A). Tgfβ1 induced a massive and dose-dependent increase of collagen α-1(I) (Col1α1) and α-Sma expression while Chrdl1 blunted this effect (FIG. 7B).

To additionally investigate the effect of Chrdl1 in the fibrotic response in vivo, the hearts of Col1α1(1)-EGFP mice (a transgenic mouse model in which EGFP is only expressed in fibroblasts (12)) were transduced with AAV2/9-control or AAV2/9-Chrdl1 and MI was induced. The hearts of Col1a1-eGFP mice overexpressing Chrdl1 showed a significantly attenuated cardiac fibrosis and reduced collagen1α1 and α-SMA expression (FIG. 7C). These data were also confirmed by q-PCR quantifying the Col1α1, α-SMA, Tgfβ1 and MMP9 transcript levels 3 days after infarction in CD1 mice (FIG. 7D).

Example 8

Expression of Chrdl1, Fam3c and Fam3b Protects Mice from Doxorubicin-Induced Cardiac Toxicity and Death Despite their efficacy as anticancer medicines, anthracyclines (including doxorubicin) can induce both acute and chronic cardiotoxicity (Swain, S. M. et al. (2003) Cancer 97: 2869-2879). In particular, cumulative doses of these drugs can cause left ventricular systolic dysfunction and heart failure. The reported incidence of ventricular dysfunction as a consequence of treatment with these drugs can be as high as approximately 10% of patients (Cardinale, D. (2015) Circulation 131: 1981-1988), with the vast majority of cases occurring within the first year of treatment. Currently, there is no standard therapy to prevent anthracycline-induced cardiotoxicity (Zamorano, J. L. et al. (2016) Eur Heart J 37: 2768-2801).

Six-week old, female C57/BL6 mice were injected intramyocardially with 30 μl of AAV9 vector preparations expressing Chrdl1, Fam3c or Fam3b using a 30G-needle syringe. One week later, doxorubicin was administered intraperitoneally at days 0, 2, 5, 8, 10 and 12 at the concentration of 4 mg/kg (cumulative dose: 24 mg/kg), according to an established protocol for chronic treatment (Li M. et al. (2018) Circulation 138: 696-711). Mice were followed with echocardiography at weeks 0, 6 and 8.

Each of Chrdl1, Fam3c and Fam3b showed strong protective activity against drug-induced death (FIG. 8A). A remarkable cardioprotective effect is observed following treatment with any of the three factors, as shown by the significant protection both against deterioration in Left Ventricle (LV) ejection fraction (FIG. 8B), and deleterious effects on LV internal diameters (FIG. 8C).

REFERENCES

1. Ruozi, G., et al. AAV-mediated in vivo functional selection of tissue-protective factors against ischaemia. *Nature communications* 6, 7388 (2015).
2. Bortolotti, F., et al. In Vivo Functional Selection Identifies Cardiotrophin-1 as a Cardiac Engraftment Factor for Mesenchymal Stromal Cells. *Circulation* 136, 1509-1524 (2017).
3. Zacchigna, S., Zentilin, L. & Giacca, M. Adeno-associated virus vectors as therapeutic and investigational tools in the cardiovascular system. *Circ Res* 114, 1827-1846 (2014).
4. Grimmond, S. M., et al. The mouse secretome: functional classification of the proteins secreted into the extracellular environment. *Genome Res* 13, 1350-1359 (2003).
5. Eulalio, A., et al. Functional screening identifies miRNAs inducing cardiac regeneration. *Nature* 492, 376-381 (2012).
6. Krijnen, P. A., et al. Apoptosis in myocardial ischaemia and infarction. *J Clin Pathol* 55, 801-811 (2002).
7. Gustafsson, A. B. & Gottlieb, R. A. Autophagy in ischemic heart disease. *Circ Res* 104, 150-158 (2009).
8. Wang, X., Guo, Z., Ding, Z. & Mehta, J. L. Inflammation, Autophagy, and Apoptosis After Myocardial Infarction. *J Am Heart Assoc* 7(2018).
9. Kimura, S., Noda, T. & Yoshimori, T. Dissection of the autophagosome maturation process by a novel reporter protein, tandem fluorescent-tagged LC3. *Autophagy* 3, 452-460 (2007).

10. Mingozzi, F., et al. Induction of immune tolerance to coagulation factor IX antigen by in vivo hepatic gene transfer. *J Clin Invest* 111, 1347-1356 (2003).
11. Bujak, M. & Frangogiannis, N. G. The role of TGF-beta signaling in myocardial infarction and cardiac remodeling. *Cardiovasc Res* 74, 184-195 (2007).
12. Zacchigna, S., et al. Paracrine effect of regulatory T cells promotes cardiomyocyte proliferation during pregnancy and after myocardial infarction. *Nature communications* 9, 2432 (2018).

All publications mentioned in the above specification are herein incorporated by reference. Various modifications and variations of the disclosed agents, compositions, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method for treating myocardial infarction, wherein the method comprises administering a polypeptide comprising the Fam3b amino acid sequence of SEQ ID NO: 3, or a polynucleotide that comprises a nucleotide sequence encoding said polypeptide, to a subject after myocardial infarction.

2. The method according to claim 1, which comprises administering the polynucleotide, wherein the polynucleotide comprises a nucleotide sequence that has at least 70% identity to SEQ ID NO: 6.

3. The method according to claim 1, wherein cardiac function is preserved after myocardial infarction or fibrosis after infarction is reduced.

4. The method according to claim 1, wherein heart failure is prevented.

5. The method according to claim 1 which comprises administering the polypeptide, wherein the polypeptide is glycosylated.

6. The method according to claim 1, wherein the polypeptide is a fusion protein.

7. The method according to claim 1 which comprises administering the polynucleotide, wherein the polynucleotide is in the form of a vector.

8. A method for treating myocardial infarction, wherein the method comprises administering a vector comprising a polynucleotide that comprises a nucleotide sequence encoding a polypeptide comprising the Fam3b amino acid sequence of SEQ ID NO: 3, to a subject after myocardial infarction.

9. The method according to claim 8, wherein the vector is a viral vector.

10. A method for treating myocardial infarction, wherein the method comprises administering a pharmaceutical composition, to a subject after myocardial infarction, wherein the pharmaceutical composition comprises a polypeptide comprising the Fam3b amino acid sequence of SEQ ID NO: 3, or a vector comprising a polynucleotide that comprises a nucleotide sequence encoding a polypeptide comprising the Fam3b amino acid sequence of SEQ ID NO: 3, and a pharmaceutically acceptable vehicle and/or excipient.

11. The method according to claim 9, wherein the viral vector is an adeno-associated viral (AAV) vector.

12. The method according to claim 1 which comprises administering the polynucleotide, wherein the polynucleotide comprises a nucleotide sequence that has at least 80% identity to SEQ ID NO: 6.

13. The method according to claim 1 which comprises administering the polynucleotide, wherein the polynucleotide comprises a nucleotide sequence that has at least 90% identity to SEQ ID NO: 6.

14. The method according to claim 1 which comprises administering the polynucleotide, wherein the polynucleotide comprises a nucleotide sequence that has at least 95% identity to SEQ ID NO: 6.

15. The method according to claim 1 which comprises administering the polynucleotide, wherein the polynucleotide comprises a nucleotide sequence that has at least 99% identity to SEQ ID NO: 6.

16. The method according to claim 1, wherein the polypeptide is an Fc fusion protein.

17. The method according to claim 1, wherein the method comprises parenterally administering the polypeptide, or wherein the method comprises parenterally administering the polynucleotide.

18. The method according to claim 1, wherein the method comprises intramyocardially administering the polypeptide, or wherein the method comprises intramyocardially administering the polynucleotide.

19. The method according to claim 1, wherein the method comprises intravenously administering the polypeptide, or wherein the method comprises intravenously administering the polynucleotide.

20. A method for treating myocardial infarction, wherein the method comprises administering a protein comprising the amino acid sequence of SEQ ID NO: 3 or SEQ ID NO: 7, or a polynucleotide that comprises a nucleotide sequence encoding said protein, to a subject after myocardial infarction.

21. The method according to claim 20 which comprises administering the protein, wherein the protein is glycosylated.

22. The method according to claim 20, wherein the protein is a fusion protein.

23. The method according to claim 20, wherein the protein is an Fc fusion protein.

24. The method according to claim 20, wherein the method comprises parenterally administering the protein, or wherein the method comprises parenterally administering the polynucleotide.

25. The method according to claim 20, wherein the method comprises intramyocardially administering the protein, or wherein the method comprises intramyocardially administering the polynucleotide.

26. The method according to claim 20, wherein the method comprises intravenously administering the protein, or wherein the method comprises intravenously administering the polynucleotide.

27. A method for preserving cardiac function and/or reducing fibrosis after myocardial infarction or cardiac toxic damage, wherein the method comprises administering a polypeptide comprising the Fam3b amino acid sequence of SEQ ID NO: 3, or a polynucleotide that comprises a nucleotide sequence encoding said polypeptide, to a subject after myocardial infarction or cardiac toxic damage.

28. The method according to claim 27 which comprises administering the polypeptide, wherein the polypeptide is glycosylated.

29. The method according to claim 27, wherein said polypeptide is a fusion protein.

30. The method according to claim 27, wherein said polypeptide is an Fc fusion protein.

31. The method according to claim 27, wherein the method comprises parenterally administering the polypeptide, or wherein the method comprises parenterally administering the polynucleotide.

32. The method according to claim 27, wherein the method comprises intramyocardially administering the polypeptide, or wherein the method comprises intramyocardially administering the polynucleotide.

33. The method according to claim 27, wherein the method comprises intravenously administering the polypeptide, or wherein the method comprises intravenously administering the polynucleotide.

34. A method for preserving cardiac function and/or reducing fibrosis after myocardial infarction or cardiac toxic damage, wherein the method comprises administering a protein comprising the amino acid sequence of SEQ ID NO: 3 or SEQ ID NO: 7, or a polynucleotide that comprises a nucleotide sequence encoding said protein, to a subject after myocardial infarction or cardiac toxic damage.

35. The method according to claim 34 which comprises administering the protein, wherein the protein is glycosylated.

36. The method according to claim 34, wherein the protein is a fusion protein.

37. The method according to claim 34, wherein the protein is an Fc fusion protein.

38. The method according to claim 34, wherein the method comprises parenterally administering the protein, or wherein the method comprises parenterally administering the polynucleotide.

39. The method according to claim 34, wherein the method comprises intramyocardially administering the protein, or wherein the method comprises intramyocardially administering the polynucleotide.

40. The method according to claim 34, wherein the method comprises intravenously administering the protein, or wherein the method comprises intravenously administering the polynucleotide.

* * * * *

SEQUENCE LISTING

```
<160> NUMBER OF SEQ ID NOS: 7

<210> SEQ ID NO 1
<211> LENGTH: 456
<212> TYPE: PRT
<213> ORGANISM: Homo sapiens

<400> SEQUENCE: 1

Met Arg Lys Lys Trp Lys Met Gly Gly Met Lys Tyr Ile Phe Ser Leu
1               5                   10                  15

Leu Phe Phe Leu Leu Leu Glu Gly Gly Lys Thr Glu Gln Val Lys His
            20                  25                  30

Ser Glu Thr Tyr Cys Met Phe Gln Asp Lys Lys Tyr Arg Val Gly Glu
        35                  40                  45

Arg Trp His Pro Tyr Leu Glu Pro Tyr Gly Leu Val Tyr Cys Val Asn
    50                  55                  60

Cys Ile Cys Ser Glu Asn Gly Asn Val Leu Cys Ser Arg Val Arg Cys
65                  70                  75                  80

Pro Asn Val His Cys Leu Ser Pro Val His Ile Pro His Leu Cys Cys
                85                  90                  95

Pro Arg Cys Pro Asp Ser Leu Pro Pro Val Asn Asn Lys Val Thr Ser
            100                 105                 110

Lys Ser Cys Glu Tyr Asn Gly Thr Thr Tyr Gln His Gly Glu Leu Phe
        115                 120                 125

Val Ala Glu Gly Leu Phe Gln Asn Arg Gln Pro Asn Gln Cys Thr Gln
    130                 135                 140

Cys Ser Cys Ser Glu Gly Asn Val Tyr Cys Gly Leu Lys Thr Cys Pro
145                 150                 155                 160

Lys Leu Thr Cys Ala Phe Pro Val Ser Val Pro Asp Ser Cys Cys Arg
                165                 170                 175

Val Cys Arg Gly Asp Gly Glu Leu Ser Trp Glu His Ser Asp Gly Asp
            180                 185                 190

Ile Phe Arg Gln Pro Ala Asn Arg Glu Ala Arg His Ser Tyr His Arg
            195                 200                 205

Ser His Tyr Asp Pro Pro Pro Ser Arg Gln Ala Gly Gly Leu Ser Arg
        210                 215                 220

Phe Pro Gly Ala Arg Ser His Arg Gly Ala Leu Met Asp Ser Gln Gln
225                 230                 235                 240

Ala Ser Gly Thr Ile Val Gln Ile Val Ile Asn Asn Lys His Lys His
                245                 250                 255

Gly Gln Val Cys Val Ser Asn Gly Lys Thr Tyr Ser His Gly Glu Ser
            260                 265                 270

Trp His Pro Asn Leu Arg Ala Phe Gly Ile Val Glu Cys Val Leu Cys
            275                 280                 285
```

-continued

```
Thr Cys Asn Val Thr Lys Gln Glu Cys Lys Lys Ile His Cys Pro Asn
    290                 295                 300

Arg Tyr Pro Cys Lys Tyr Pro Gln Lys Ile Asp Gly Lys Cys Cys Lys
305                 310                 315                 320

Val Cys Pro Gly Lys Lys Ala Lys Glu Leu Pro Gly Gln Ser Phe Asp
                325                 330                 335

Asn Lys Gly Tyr Phe Cys Gly Glu Glu Thr Met Pro Val Tyr Glu Ser
                340                 345                 350

Val Phe Met Glu Asp Gly Glu Thr Thr Arg Lys Ile Ala Leu Glu Thr
                355                 360                 365

Glu Arg Pro Pro Gln Val Glu Val His Val Trp Thr Ile Arg Lys Gly
    370                 375                 380

Ile Leu Gln His Phe His Ile Glu Lys Ile Ser Lys Arg Met Phe Glu
385                 390                 395                 400

Glu Leu Pro His Phe Lys Leu Val Thr Arg Thr Thr Leu Ser Gln Trp
                405                 410                 415

Lys Ile Phe Thr Glu Gly Glu Ala Gln Ile Ser Gln Met Cys Ser Ser
                420                 425                 430

Arg Val Cys Arg Thr Glu Leu Glu Asp Leu Val Lys Val Leu Tyr Leu
                435                 440                 445

Glu Arg Ser Glu Lys Gly His Cys
    450                 455
```

```
<210> SEQ ID NO 2
<211> LENGTH: 227
<212> TYPE: PRT
<213> ORGANISM: Homo sapiens

<400> SEQUENCE: 2

Met Arg Val Ala Gly Ala Ala Lys Leu Val Val Ala Val Ala Val Phe
1                 5                  10                  15

Leu Leu Thr Phe Tyr Val Ile Ser Gln Val Phe Glu Ile Lys Met Asp
                20                  25                  30

Ala Ser Leu Gly Asn Leu Phe Ala Arg Ser Ala Leu Asp Thr Ala Ala
                35                  40                  45

Arg Ser Thr Lys Pro Pro Arg Tyr Lys Cys Gly Ile Ser Lys Ala Cys
    50                  55                  60

Pro Glu Lys His Phe Ala Phe Lys Met Ala Ser Gly Ala Ala Asn Val
65                  70                  75                  80

Val Gly Pro Lys Ile Cys Leu Glu Asp Asn Val Leu Met Ser Gly Val
                85                  90                  95

Lys Asn Asn Val Gly Arg Gly Ile Asn Val Ala Leu Ala Asn Gly Lys
                100                 105                 110

Thr Gly Glu Val Leu Asp Thr Lys Tyr Phe Asp Met Trp Gly Gly Asp
                115                 120                 125

Val Ala Pro Phe Ile Glu Phe Leu Lys Ala Ile Gln Asp Gly Thr Ile
    130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
                180                 185                 190

Lys Ser Pro Phe Glu Gln His Ile Lys Asn Asn Lys Asp Thr Asn Lys
```

-continued
─────────────────────────────────────────────────────────────────────

```
              195                 200                 205
Tyr Glu Gly Trp Pro Glu Val Val Glu Met Glu Gly Cys Ile Pro Gln
    210                 215                 220

Lys Gln Asp
225

<210> SEQ ID NO 3
<211> LENGTH: 235
<212> TYPE: PRT
<213> ORGANISM: Homo sapiens

<400> SEQUENCE: 3

Met Arg Pro Leu Ala Gly Gly Leu Leu Lys Val Val Phe Val Val Phe
1               5                   10                  15

Ala Ser Leu Cys Ala Trp Tyr Ser Gly Tyr Leu Leu Ala Glu Leu Ile
        20                  25                  30

Pro Asp Ala Pro Leu Ser Ser Ala Ala Tyr Ser Ile Arg Ser Ile Gly
        35                  40                  45

Glu Arg Pro Val Leu Lys Ala Pro Val Pro Lys Arg Gln Lys Cys Asp
    50                  55                  60

His Trp Thr Pro Cys Pro Ser Asp Thr Tyr Ala Tyr Arg Leu Leu Ser
65                  70                  75                  80

Gly Gly Gly Arg Ser Lys Tyr Ala Lys Ile Cys Phe Glu Asp Asn Leu
                85                  90                  95

Leu Met Gly Glu Gln Leu Gly Asn Val Ala Arg Gly Ile Asn Ile Ala
            100                 105                 110

Ile Val Asn Tyr Val Thr Gly Asn Val Thr Ala Thr Arg Cys Phe Asp
        115                 120                 125

Met Tyr Glu Gly Asp Asn Ser Gly Pro Met Thr Lys Phe Ile Gln Ser
    130                 135                 140

Ala Ala Pro Lys Ser Leu Leu Phe Met Val Thr Tyr Asp Asp Gly Ser
145                 150                 155                 160

Thr Arg Leu Asn Asn Asp Ala Lys Asn Ala Ile Glu Ala Leu Gly Ser
                165                 170                 175

Lys Glu Ile Arg Asn Met Lys Phe Arg Ser Ser Trp Val Phe Ile Ala
            180                 185                 190

Ala Lys Gly Leu Glu Leu Pro Ser Glu Ile Gln Arg Glu Lys Ile Asn
            195                 200                 205

His Ser Asp Ala Lys Asn Asn Arg Tyr Ser Gly Trp Pro Ala Glu Ile
    210                 215                 220

Gln Ile Glu Gly Cys Ile Pro Lys Glu Arg Ser
225                 230                 235

<210> SEQ ID NO 4
<211> LENGTH: 1377
<212> TYPE: DNA
<213> ORGANISM: Homo sapiens

<400> SEQUENCE: 4
atgagaaaaa agtggaaaat gggaggcatg aaatacatct tttcgttgtt gttctttctt      60
ttgctagaag gaggcaaaac agagcaagta aaacattcag agacatattg catgtttcaa     120
gacaagaagt acagagtggg tgagagatgg catccttacc tggaacctta tgggttggtt     180
tactgcgtga actgcatctg ctcagagaat gggaatgtgc tttgcagccg agtcagatgt     240
ccaaatgttc attgcctttc tcctgtgcat attcctcatc tgtgctgccc tcgctgccca     300
```

```
gaagactcct tacccccagt gaacaataag gtgaccagca agtcttgcga gtacaatggg      360
acaacttacc aacatggaga gctgttcgta gctgaagggc tctttcagaa tcggcaaccc      420
aatcaatgca cccagtgcag ctgttcggag ggaaacgtgt attgtggtct caagacttgc      480
cccaaattaa cctgtgcctt cccagtctct gttccagatt cctgctgccg ggtatgcaga      540
ggagatggag aactgtcatg ggaacattct gatggtgata tcttccggca acctgccaac      600
agagaagcaa gacattctta ccaccgctct cactatgatc ctccaccaag ccgacaggct      660
ggaggtctgt cccgctttcc tggggccaga agtcaccggg gagctcttat ggattcccag      720
caagcatcag gaaccattgt gcaaattgtc atcaataaca aacacaagca tggacaagtg      780
tgtgtttcca atggaaagac ctattctcat ggcgagtcct ggcacccaaa cctccgggca      840
tttggcattg tggagtgtgt gctatgtact tgtaatgtca ccaagcaaga gtgtaagaaa      900
atccactgcc ccaatcgata cccctgcaag tatcctcaaa aaatagacgg aaaatgctgc      960
aaggtgtgtc caggtaaaaa agcaaaagaa gaacttccag gccaaagctt tgacaataaa      1020
ggctacttct gcggggaaga aacgatgcct gtgtatgagt ctgtattcat ggaggatggg      1080
gagacaacca gaaaaatagc actggagact gagagaccac ctcaggtaga ggtccacgtt      1140
tggactattc gaaagggcat tctccagcac ttccatattg agaagatctc caagaggatg      1200
tttgaggagc ttcctcactt caagctggtg accagaacaa ccctgagcca gtggaagatc      1260
ttcaccgaag agaagctca gatcagccag atgtgttcaa gtcgtgtatg cagaacagag      1320
cttgaagatt tagtcaaggt tttgtacctg agagatctg aaaagggcca ctgttag       1377
```

<210> SEQ ID NO 5
<211> LENGTH: 684
<212> TYPE: DNA
<213> ORGANISM: Homo sapiens

<400> SEQUENCE: 5

```
atgagggtag caggtgctgc aaagttggtg gtagctgtgg cagtgttttt actgacattt      60
tatgttattt ctcaagtatt tgaaataaaa atggatgcaa gtttaggaaa tctatttgca      120
agatcagcat tggacacagc tgcacgttct acaaagcctc ccagatataa gtgtgggatc      180
tcaaaagctt gccctgagaa gcattttgct tttaaaatgg caagtggagc agccaacgtg      240
gtgggaccca aaatctgcct ggaagataat gtttttaatga gtggtgttaa gaataatgtt      300
ggaagaggga tcaatgttgc cttggcaaat ggaaaaacag gagaagtatt agacactaaa      360
tattttgaca tgtggggagg agatgtggca ccatttattg agtttctgaa ggccatacaa      420
gatggaacaa tagtttttaat gggaacatac gatgatggag caaccaaact caatgatgag      480
gcacggcggc tcattgctga tttggggagc acatctatta ctaatcttgg ttttagagac      540
aactgggtct tctgtggtgg aagggcatt aagacaaaaa gccctttga acagcacata      600 aagaacaata aggatacaaa caaatatgaa ggatggcctg aagttgtaga aatggaagga      660
tgcatccccc agaagcaaga ctaa                                          684
```

<210> SEQ ID NO 6
<211> LENGTH: 708
<212> TYPE: DNA
<213> ORGANISM: Homo sapiens

<400> SEQUENCE: 6

```
atgcgcccat ggctggtggg cctgctcaag gtggtgttcg tggtcttcgc ctccttgtgt      60
gcctggtatt cggggtacct gctcgcagag ctcattccag atgcacccct gtccagtgct      120
```

-continued

```
gcctatagca tccgcagcat cggggagagg cctgtcctca aagctccagt ccccaaaagg    180
caaaaatgtg accactggac tccctgccca tctgacacct atgcctacag gttactcagc    240
ggaggtggca gaagcaagta cgccaaaatc tgctttgagg ataacctact tatgggagaa    300
cagctgggaa atgttgccag aggaataaac attgccattg tcaactatgt aactgggaat    360
gtgacagcaa cacgatgttt tgatatgtat gaaggtgata actctggacc gatgacaaag    420
tttattcaga gtgctgctcc aaaatccctg ctcttcatgg tgacctatga cgacggaagc    480
acaagactga ataacgatgc caagaatgcc atagaagcac ttggaagtaa agaaatcagg    540
aacatgaaat tcaggtctag ctgggtattt attgcagcaa aaggcttgga actcccttcc    600
gaaattcaga gagaaaagat caaccactct gatgctaaga acaacagata ttctggctgg    660
cctgcagaga tccagataga aggctgcata cccaaagaac gaagctga             708
```

<210> SEQ ID NO 7
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 7

```
Glu Leu Ile Pro Asp Ala Pro Leu Ser Ser Ala Ala Tyr Ser Ile Arg
1               5                   10                  15

Ser Ile Gly Glu Arg Pro Val Leu Lys Ala Pro Val Pro Lys Arg Gln
                20                  25                  30

Lys Cys Asp His Trp Thr Pro Cys Pro Ser Asp Thr Tyr Ala Tyr Arg
            35                  40                  45

Leu Leu Ser Gly Gly Gly Arg Ser Lys Tyr Ala Lys Ile Cys Phe Glu
        50                  55                  60

Asp Asn Leu Leu Met Gly Glu Gln Leu Gly Asn Val Ala Arg Gly Ile
65                  70                  75                  80

Asn Ile Ala Ile Val Asn Tyr Val Thr Gly Asn Val Thr Ala Thr Arg
                85                  90                  95

Cys Phe Asp Met Tyr Glu Gly Asp Asn Ser Gly Pro Met Thr Lys Phe
                100                 105                 110

Ile Gln Ser Ala Ala Pro Lys Ser Leu Leu Phe Met Val Thr Tyr Asp
            115                 120                 125

Asp Gly Ser Thr Arg Leu Asn Asn Asp Ala Lys Asn Ala Ile Glu Ala
        130                 135                 140

Leu Gly Ser Lys Glu Ile Arg Asn Met Lys Phe Arg Ser Ser Trp Val
145                 150                 155                 160

Phe Ile Ala Ala Lys Gly Leu Glu Leu Pro Ser Glu Ile Gln Arg Glu
                165                 170                 175

Lys Ile Asn His Ser Asp Ala Lys Asn Asn Arg Tyr Ser Gly Trp Pro
                180                 185                 190

Ala Glu Ile Gln Ile Glu Gly Cys Ile Pro Lys Glu Arg Ser
        195                 200                 205
```